(12) United States Patent
Tokish, Jr. et al.

(10) Patent No.: US 8,187,303 B2
(45) Date of Patent: *May 29, 2012

(54) ANTI-ROTATION FIXATION ELEMENT FOR SPINAL PROSTHESES

(75) Inventors: Leonard J. Tokish, Jr., Issaquah, WA (US); Mark T. Charbonneau, Bellevue, WA (US); Mark A. Reiley, Piedmont, CA (US); Robert M. Scribner, Niwot, CO (US)

(73) Assignee: GMEDelaware 2 LLC, Audubon, PA (US)

( * ) Notice: Subject to any disclaimer, the term of this patent is extended or adjusted under 35 U.S.C. 154(b) by 1726 days.

This patent is subject to a terminal disclaimer.

(21) Appl. No.: 10/831,657

(22) Filed: Apr. 22, 2004

(65) Prior Publication Data

US 2005/0240264 A1   Oct. 27, 2005

(51) Int. Cl.
*A61B 17/70* (2006.01)
*A61F 2/44* (2006.01)

(52) U.S. Cl. .................. 606/247; 623/17.11

(58) Field of Classification Search ..... 623/17.11–17.16
See application file for complete search history.

(56) References Cited

U.S. PATENT DOCUMENTS

| | | |
|---|---|---|
| 1,308,451 A | 7/1919 | Schachat |
| 2,502,902 A | 4/1950 | Tofflemire |
| 2,930,133 A | 3/1960 | Thompson |
| 2,959,861 A | 11/1960 | Stromquist |
| 3,596,656 A | 8/1971 | Kaute |
| 3,710,789 A | 1/1973 | Ersek |
| 3,726,279 A | 4/1973 | Barefoot et al. |
| 3,867,728 A | 2/1975 | Stubstad et al. |
| 3,875,595 A | 4/1975 | Froning |
| 3,941,127 A | 3/1976 | Froning |
| 4,040,130 A | 8/1977 | Laure |
| 4,123,848 A | 11/1978 | Emmerich et al. |
| 4,156,296 A | 5/1979 | Johnson et al. |
| 4,210,317 A | 7/1980 | Spann et al. |
| 4,231,121 A | 11/1980 | Lewis |
| 4,271,836 A | 6/1981 | Bacal et al. |
| 4,349,921 A | 9/1982 | Kuntz |
| 4,394,370 A | 7/1983 | Jefferies |
| 4,472,840 A | 9/1984 | Jefferies |
| 4,502,161 A | 3/1985 | Wall |
| 4,554,914 A | 11/1985 | Kapp et al. |
| 4,611,581 A | 9/1986 | Steffee |
| 4,633,722 A | 1/1987 | Beardmore et al. |

(Continued)

FOREIGN PATENT DOCUMENTS

DE   10135771 A1   2/2003

(Continued)

OTHER PUBLICATIONS

Abraham, D.J. et al. Indications and Trends in Use in Cervical Spinal Fusions. *Orthop Clin North Am.* Oct. 1998; 29(4):731-44.

(Continued)

*Primary Examiner* — Anu Ramana

(57) ABSTRACT

Prostheses, systems, and methods are provided for replacement of natural facet joints between adjacent vertebrae with vertebral prostheses. A portion of the vertebral prosthesis includes anti-rotation and/or anti-pullout elements to prevent or reduce prosthesis fastener rotation or pull out as a result of torques applied to the prosthesis. Various tools and methods aid the process of surgically adding the vertebral prosthesis to a patient's vertebra.

20 Claims, 24 Drawing Sheets

U.S. PATENT DOCUMENTS

| | | |
|---|---|---|
| 4,693,722 A | 9/1987 | Wall |
| 4,697,582 A | 10/1987 | William |
| 4,710,075 A | 12/1987 | Davison |
| 4,759,769 A | 7/1988 | Hedman et al. |
| 4,772,287 A | 9/1988 | Ray et al. |
| 4,778,472 A | 10/1988 | Homsy et al. |
| 4,795,469 A | 1/1989 | Oh |
| 4,805,602 A | 2/1989 | Puno et al. |
| 4,863,477 A | 9/1989 | Monson |
| 4,904,260 A | 2/1990 | Ray et al. |
| 4,911,718 A | 3/1990 | Lee et al. |
| 4,917,701 A | 4/1990 | Morgan |
| 4,932,975 A | 6/1990 | Main et al. |
| 4,950,270 A | 8/1990 | Bowman et al. |
| 4,955,916 A | 9/1990 | Carignan et al. |
| 4,957,495 A | 9/1990 | Kluger |
| 4,987,904 A | 1/1991 | Wilson |
| 5,000,165 A | 3/1991 | Watanabe |
| 5,015,255 A | 5/1991 | Kuslich |
| 5,019,081 A | 5/1991 | Watanabe |
| 5,047,055 A | 9/1991 | Bao et al. |
| 5,062,845 A | 11/1991 | Kuslich et al. |
| 5,070,623 A | 12/1991 | Barnes |
| 5,071,437 A | 12/1991 | Steffee |
| 5,092,866 A | 3/1992 | Breard et al. |
| 5,098,434 A | 3/1992 | Serbousek |
| 5,108,399 A | 4/1992 | Eitenmuller et al. |
| 5,129,900 A | 7/1992 | Asher et al. |
| 5,147,361 A | 9/1992 | Ojima et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,261,910 A | 11/1993 | Warden et al. |
| 5,284,655 A | 2/1994 | Bogdansky et al. |
| 5,300,073 A | 4/1994 | Ray et al. |
| 5,303,480 A | 4/1994 | Chek |
| 5,306,308 A | 4/1994 | Gross et al. |
| 5,306,309 A | 4/1994 | Wagner et al. |
| 5,312,409 A | 5/1994 | McLaughlin et al. |
| 5,314,429 A | 5/1994 | Goble |
| 5,314,476 A | 5/1994 | Prewett et al. |
| 5,314,486 A | 5/1994 | Zang et al. |
| 5,314,489 A | 5/1994 | Hoffman et al. |
| 5,314,492 A | 5/1994 | Hamilton et al. |
| 5,329,933 A | 7/1994 | Graf |
| 5,334,203 A | 8/1994 | Wagner |
| 5,348,026 A | 9/1994 | Davidson |
| 5,350,380 A | 9/1994 | Goble et al. |
| 5,360,448 A | 11/1994 | Thramann |
| 5,366,455 A | 11/1994 | Dove et al. |
| 5,370,697 A | 12/1994 | Baumgartner |
| 5,401,269 A | 3/1995 | Buttner-Janz et al. |
| 5,405,390 A | 4/1995 | O'Leary et al. |
| 5,413,576 A | 5/1995 | Rivard |
| 5,415,659 A | 5/1995 | Lee et al. |
| 5,415,661 A | 5/1995 | Holmes |
| 5,425,773 A | 6/1995 | Boyd et al. |
| 5,437,669 A | 8/1995 | Yuan et al. |
| 5,437,672 A | 8/1995 | Alleyne |
| 5,443,483 A | 8/1995 | Kirsch |
| 5,445,639 A | 8/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,470,333 A | 11/1995 | Ray |
| 5,474,551 A | 12/1995 | Finn et al. |
| 5,474,555 A | 12/1995 | Puno et al. |
| 5,491,882 A | 2/1996 | Walston et al. |
| 5,496,318 A | 3/1996 | Howland et al. |
| 5,501,684 A | 3/1996 | Schlapfer et al. |
| 5,507,745 A | 4/1996 | Logroscino et al. |
| 5,507,823 A | 4/1996 | Walston et al. |
| 5,510,396 A | 4/1996 | Prewett et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,569,247 A | 10/1996 | Morrison |
| 5,571,189 A | 11/1996 | Kuslich |
| 5,571,191 A | 11/1996 | Fitz |
| 5,575,792 A | 11/1996 | Errico et al. |
| 5,577,995 A | 11/1996 | Walker et al. |
| 5,587,695 A | 12/1996 | Warmerdam |
| 5,599,311 A | 2/1997 | Raulerson |
| 5,603,713 A | 2/1997 | Aust et al. |
| 5,609,641 A | 3/1997 | Johnson et al. |
| 5,643,263 A | 7/1997 | Simonson |
| 5,645,597 A | 7/1997 | Krapiva |
| 5,645,599 A | 7/1997 | Samani |
| 5,649,930 A | 7/1997 | Kertzner |
| 5,653,762 A | 8/1997 | Pisharodi |
| 5,658,338 A | 8/1997 | Tullos et al. |
| 5,662,651 A | 9/1997 | Tornier et al. |
| 5,672,175 A | 9/1997 | Martin |
| 5,674,295 A | 10/1997 | Ray et al. |
| 5,674,296 A | 10/1997 | Bryan et al. |
| 5,676,701 A | 10/1997 | Yuan et al. |
| 5,678,317 A | 10/1997 | Stefanakos |
| 5,683,391 A | 11/1997 | Boyd |
| 5,683,392 A | 11/1997 | Richelsoph et al. |
| 5,683,464 A | 11/1997 | Wagner et al. |
| 5,683,466 A | 11/1997 | Vitale |
| 5,688,274 A | 11/1997 | Errico et al. |
| 5,690,630 A | 11/1997 | Errico et al. |
| 5,700,268 A | 12/1997 | Bertin |
| 5,702,450 A | 12/1997 | Bisserie |
| 5,702,452 A | 12/1997 | Argenson et al. |
| 5,704,941 A | 1/1998 | Jacober et al. |
| 5,713,900 A | 2/1998 | Benzel et al. |
| 5,716,415 A | 2/1998 | Steffee |
| 5,725,527 A | 3/1998 | Biedermann et al. |
| 5,733,284 A | 3/1998 | Martin |
| 5,738,585 A | 4/1998 | Hoyt, III et al. |
| 5,741,255 A | 4/1998 | Krag et al. |
| 5,741,261 A | 4/1998 | Moskovitz et al. |
| 5,766,253 A | 6/1998 | Brosnahan, III |
| 5,776,135 A | 7/1998 | Errico et al. |
| 5,782,833 A | 7/1998 | Haider |
| 5,797,911 A | 8/1998 | Sherman et al. |
| 5,800,433 A | 9/1998 | Benzel et al. |
| 5,824,093 A | 10/1998 | Ray et al. |
| 5,824,094 A | 10/1998 | Serhan et al. |
| 5,827,289 A | 10/1998 | Reiley et al. |
| 5,836,948 A | 11/1998 | Zucherman et al. |
| 5,860,977 A | 1/1999 | Zucherman et al. |
| 5,863,293 A | 1/1999 | Richelsoph |
| 5,865,846 A | 2/1999 | Bryan et al. |
| 5,866,113 A | 2/1999 | Hendriks et al. |
| 5,868,745 A | 2/1999 | Alleyne |
| 5,879,350 A | 3/1999 | Sherman et al. |
| 5,879,396 A | 3/1999 | Walston et al. |
| 5,885,285 A | 3/1999 | Simonson |
| 5,885,286 A | 3/1999 | Sherman et al. |
| 5,891,145 A | 4/1999 | Morrison et al. |
| 5,893,889 A | 4/1999 | Harrington |
| RE36,221 E | 6/1999 | Breard et al. |
| 5,947,893 A | 9/1999 | Agrawal et al. |
| 5,947,965 A | 9/1999 | Bryan |
| 5,964,760 A | 10/1999 | Richelsoph |
| 5,984,926 A * | 11/1999 | Jones .................. 606/322 |
| 6,001,130 A | 12/1999 | Bryan et al. |
| 6,004,353 A | 12/1999 | Masini |
| 6,010,503 A | 1/2000 | Richelsoph et al. |
| 6,014,588 A | 1/2000 | Fitz |
| 6,019,759 A | 2/2000 | Rogozinski |
| 6,019,792 A | 2/2000 | Cauthen |
| 6,022,350 A | 2/2000 | Ganem |
| 6,039,763 A | 3/2000 | Shelokov |
| 6,048,342 A | 4/2000 | Zucherman et al. |
| 6,050,997 A | 4/2000 | Mullane |
| 6,053,917 A | 4/2000 | Sherman et al. |
| 6,063,121 A | 5/2000 | Xavier et al. |
| 6,066,325 A | 5/2000 | Wallace et al. |

| | | | |
|---|---|---|---|
| 6,068,630 A | 5/2000 | Zucherman et al. | |
| RE36,758 E | 6/2000 | Fitz | |
| 6,074,391 A | 6/2000 | Metz-Stavenhagen et al. | |
| 6,077,262 A | 6/2000 | Schläpfer et al. | |
| 6,080,157 A | 6/2000 | Cathro et al. | |
| 6,086,590 A | 7/2000 | Margulies et al. | |
| 6,090,111 A | 7/2000 | Nichols | |
| 6,113,600 A | 9/2000 | Drummond et al. | |
| 6,113,637 A | 9/2000 | Gill et al. | |
| 6,120,510 A | 9/2000 | Albrektsson et al. | |
| 6,132,430 A | 10/2000 | Wagner | |
| 6,132,462 A | 10/2000 | Li | |
| 6,132,464 A | 10/2000 | Martin | |
| 6,132,465 A | 10/2000 | Ray et al. | |
| 6,165,177 A | 12/2000 | Wilson et al. | |
| 6,190,388 B1 | 2/2001 | Michelson et al. | |
| 6,193,724 B1 | 2/2001 | Chan | |
| 6,193,758 B1 | 2/2001 | Huebner | |
| 6,200,322 B1 | 3/2001 | Branch et al. | |
| 6,214,012 B1 | 4/2001 | Karpman et al. | |
| 6,224,602 B1 | 5/2001 | Hayes | |
| 6,228,085 B1 | 5/2001 | Theken et al. | |
| 6,231,575 B1 | 5/2001 | Krag | |
| 6,248,105 B1 | 6/2001 | Schläpfer et al. | |
| 6,280,443 B1 | 8/2001 | Gu et al. | |
| 6,290,703 B1 | 9/2001 | Ganem | |
| 6,293,949 B1 | 9/2001 | Justis et al. | |
| 6,302,890 B1 | 10/2001 | Leone, Jr. | |
| 6,309,391 B1 | 10/2001 | Crandall et al. | |
| 6,312,431 B1 | 11/2001 | Asfora | |
| 6,340,361 B1 | 1/2002 | Kraus et al. | |
| 6,340,477 B1 | 1/2002 | Anderson | |
| 6,342,054 B1 | 1/2002 | Mata | |
| 6,361,506 B1 | 3/2002 | Saenger et al. | |
| 6,368,320 B1 | 4/2002 | Le Couedic et al. | |
| 6,419,703 B1 | 7/2002 | Fallin et al. | |
| 6,440,169 B1 | 8/2002 | Elberg et al. | |
| 6,443,954 B1 | 9/2002 | Bramlet et al. | |
| 6,451,021 B1 | 9/2002 | Ralph et al. | |
| 6,471,705 B1 | 10/2002 | Biedermann et al. | |
| 6,514,253 B1 | 2/2003 | Yao | |
| 6,520,963 B1 | 2/2003 | McKinley | |
| 6,524,315 B1 | 2/2003 | Selvitelli et al. | |
| 6,540,749 B2 | 4/2003 | Schäfer et al. | |
| 6,547,790 B2 | 4/2003 | Harkey, III et al. | |
| 6,554,843 B1 | 4/2003 | Ou | |
| 6,565,565 B1 | 5/2003 | Yuan et al. | |
| 6,565,572 B2 * | 5/2003 | Chappius | 600/300 |
| 6,565,605 B2 | 5/2003 | Goble et al. | |
| 6,572,617 B1 | 6/2003 | Senegas | |
| 6,579,319 B2 | 6/2003 | Goble et al. | |
| 6,585,740 B2 | 7/2003 | Schlapfer et al. | |
| 6,585,769 B1 | 7/2003 | Muhanna et al. | |
| 6,607,530 B1 | 8/2003 | Carl et al. | |
| 6,610,091 B1 | 8/2003 | Reiley | |
| 6,619,091 B2 | 9/2003 | Heffe | |
| 6,623,485 B2 | 9/2003 | Doubler et al. | |
| 6,626,909 B2 | 9/2003 | Chin | |
| 6,632,226 B2 | 10/2003 | Chan | |
| 6,638,281 B2 | 10/2003 | Gorek | |
| 6,645,214 B2 | 11/2003 | Brown et al. | |
| 6,648,891 B2 | 11/2003 | Kim | |
| 6,669,698 B1 | 12/2003 | Tromanhauser et al. | |
| 6,669,729 B2 | 12/2003 | Chin | |
| 6,712,818 B1 | 3/2004 | Michelson | |
| 6,712,849 B2 | 3/2004 | Re et al. | |
| 6,736,815 B2 | 5/2004 | Ginn | |
| 6,749,361 B2 | 6/2004 | Hermann et al. | |
| 6,761,698 B2 | 7/2004 | Shibata et al. | |
| 6,761,720 B1 | 7/2004 | Senegas | |
| 6,770,095 B2 | 8/2004 | Grinberg et al. | |
| 6,783,527 B2 | 8/2004 | Drewry et al. | |
| 6,790,233 B2 | 9/2004 | Brodke et al. | |
| 6,793,678 B2 | 9/2004 | Hawkins | |
| 6,802,844 B2 | 10/2004 | Ferree | |
| 6,811,567 B2 | 11/2004 | Reiley | |
| 6,902,567 B2 * | 6/2005 | Del Medico | 606/71 |
| 6,902,580 B2 | 6/2005 | Fallin et al. | |
| 6,908,465 B2 * | 6/2005 | von Hoffmann et al. | 606/67 |
| 6,949,123 B2 | 9/2005 | Reiley | |
| 6,974,478 B2 | 12/2005 | Reiley et al. | |
| 6,979,299 B2 | 12/2005 | Peabody et al. | |
| 7,011,658 B2 | 3/2006 | Young | |
| 7,044,969 B2 | 5/2006 | Errico et al. | |
| 7,051,451 B2 | 5/2006 | Augostino et al. | |
| 7,220,262 B1 | 5/2007 | Hynes | |
| 7,294,127 B2 | 11/2007 | Leung et al. | |
| 7,302,288 B1 | 11/2007 | Schellenberg | |
| 7,309,338 B2 | 12/2007 | Cragg | |
| 7,445,635 B2 | 11/2008 | Fallin et al. | |
| 7,455,685 B2 | 11/2008 | Justis | |
| 7,547,324 B2 | 6/2009 | Cragg et al. | |
| 2001/0012938 A1 | 8/2001 | Zucherman et al. | |
| 2001/0020170 A1 | 9/2001 | Zucherman et al. | |
| 2002/0013585 A1 | 1/2002 | Gournay et al. | |
| 2002/0013588 A1 | 1/2002 | Landry et al. | |
| 2002/0029039 A1 | 3/2002 | Zucherman et al. | |
| 2002/0042613 A1 | 4/2002 | Mata | |
| 2002/0049446 A1 | 4/2002 | Harkey, III et al. | |
| 2002/0052603 A1 | 5/2002 | Nichols et al. | |
| 2002/0065557 A1 | 5/2002 | Goble et al. | |
| 2002/0068975 A1 | 6/2002 | Teitelbaum et al. | |
| 2002/0082601 A1 | 6/2002 | Toyama et al. | |
| 2002/0120272 A1 | 8/2002 | Yuan et al. | |
| 2002/0123752 A1 | 9/2002 | Schultheiss et al. | |
| 2002/0123806 A1 | 9/2002 | Reiley | |
| 2002/0151895 A1 | 10/2002 | Soboleski et al. | |
| 2003/0004572 A1 | 1/2003 | Goble et al. | |
| 2003/0028250 A1 | 2/2003 | Reiley et al. | |
| 2003/0040797 A1 | 2/2003 | Fallin et al. | |
| 2003/0055427 A1 | 3/2003 | Graf | |
| 2003/0069603 A1 * | 4/2003 | Little et al. | 606/219 |
| 2003/0125740 A1 | 7/2003 | Khanna | |
| 2003/0153912 A1 | 8/2003 | Graf | |
| 2003/0181914 A1 | 9/2003 | Johnson et al. | |
| 2003/0191532 A1 | 10/2003 | Goble et al. | |
| 2003/0195631 A1 | 10/2003 | Ferree | |
| 2003/0204259 A1 | 10/2003 | Goble et al. | |
| 2003/0204261 A1 | 10/2003 | Eisermann et al. | |
| 2003/0233148 A1 | 12/2003 | Ferree | |
| 2004/0006391 A1 | 1/2004 | Reiley | |
| 2004/0049205 A1 | 3/2004 | Lee et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0059429 A1 | 3/2004 | Amin et al. | |
| 2004/0111154 A1 | 6/2004 | Reiley | |
| 2004/0116927 A1 | 6/2004 | Graf | |
| 2004/0127989 A1 | 7/2004 | Dooris et al. | |
| 2004/0143264 A1 | 7/2004 | McAfee | |
| 2004/0204710 A1 | 10/2004 | Patel et al. | |
| 2004/0204718 A1 | 10/2004 | Hoffman | |
| 2004/0230201 A1 | 11/2004 | Yuan et al. | |
| 2004/0230304 A1 | 11/2004 | Yuan et al. | |
| 2004/0260305 A1 | 12/2004 | Gorensek et al. | |
| 2005/0010291 A1 | 1/2005 | Stinson et al. | |
| 2005/0015146 A1 | 1/2005 | Louis et al. | |
| 2005/0027359 A1 | 2/2005 | Mashburn | |
| 2005/0027361 A1 | 2/2005 | Reiley | |
| 2005/0033431 A1 | 2/2005 | Gordon et al. | |
| 2005/0033432 A1 | 2/2005 | Gordon et al. | |
| 2005/0033434 A1 | 2/2005 | Berry | |
| 2005/0033439 A1 | 2/2005 | Gordon et al. | |
| 2005/0043799 A1 | 2/2005 | Reiley | |
| 2005/0049705 A1 | 3/2005 | Hale et al. | |
| 2005/0055096 A1 | 3/2005 | Serhan et al. | |
| 2005/0059972 A1 | 3/2005 | Biscup | |
| 2005/0080428 A1 | 4/2005 | White | |
| 2005/0085912 A1 | 4/2005 | Arnin et al. | |
| 2005/0101956 A1 | 5/2005 | Simonson | |
| 2005/0102028 A1 | 5/2005 | Arnin et al. | |
| 2005/0119748 A1 | 6/2005 | Reiley et al. | |
| 2005/0131406 A1 | 6/2005 | Reiley et al. | |

| | | | |
|---|---|---|---|
| 2005/0131409 A1 | 6/2005 | Chervitz et al. | |
| 2005/0131537 A1 | 6/2005 | Hoy et al. | |
| 2005/0131538 A1 | 6/2005 | Chervitz et al. | |
| 2005/0131545 A1 | 6/2005 | Chervitz et al. | |
| 2005/0137705 A1 | 6/2005 | Reiley | |
| 2005/0137706 A1 | 6/2005 | Reiley | |
| 2005/0143818 A1 | 6/2005 | Yuan et al. | |
| 2005/0149190 A1 | 7/2005 | Reiley | |
| 2005/0159746 A1 | 7/2005 | Grob et al. | |
| 2005/0165484 A1 | 7/2005 | Ferree | |
| 2005/0177240 A1 | 8/2005 | Blain | |
| 2005/0187560 A1 | 8/2005 | Dietzel et al. | |
| 2005/0192589 A1 | 9/2005 | Raymond et al. | |
| 2005/0203532 A1 | 9/2005 | Ferguson et al. | |
| 2005/0203533 A1 | 9/2005 | Ferguson et al. | |
| 2005/0222683 A1 | 10/2005 | Berry | |
| 2005/0228500 A1 | 10/2005 | Kim et al. | |
| 2005/0234552 A1 | 10/2005 | Reiley | |
| 2005/0235508 A1 | 10/2005 | Augostino et al. | |
| 2005/0240265 A1 | 10/2005 | Kuiper et al. | |
| 2005/0240266 A1 | 10/2005 | Kuiper et al. | |
| 2005/0251256 A1 | 11/2005 | Reiley | |
| 2005/0261770 A1 | 11/2005 | Kuiper et al. | |
| 2005/0267579 A1 | 12/2005 | Reiley et al. | |
| 2005/0283238 A1 | 12/2005 | Reiley | |
| 2006/0009847 A1 | 1/2006 | Reiley | |
| 2006/0009848 A1 | 1/2006 | Reiley | |
| 2006/0009849 A1 | 1/2006 | Reiley | |
| 2006/0029186 A1 | 2/2006 | De Villiers et al. | |
| 2006/0041311 A1 | 2/2006 | McLeer | |
| 2006/0052785 A1 | 3/2006 | Augostino et al. | |
| 2006/0058791 A1 | 3/2006 | Broman et al. | |
| 2006/0079895 A1 | 4/2006 | McLeer | |
| 2006/0085072 A1 | 4/2006 | Funk et al. | |
| 2006/0085075 A1 | 4/2006 | McLeer | |
| 2006/0100707 A1 | 5/2006 | Stinson et al. | |
| 2006/0100709 A1 | 5/2006 | Reiley | |
| 2006/0122703 A1 | 6/2006 | Aebi et al. | |
| 2006/0149375 A1 | 7/2006 | Yuan et al. | |
| 2006/0184180 A1 | 8/2006 | Augostino et al. | |
| 2006/0241532 A1 | 10/2006 | Murakami et al. | |
| 2006/0265070 A1 | 11/2006 | Stinson et al. | |
| 2007/0079517 A1 | 4/2007 | Augostino et al. | |
| 2007/0088358 A1 | 4/2007 | Yuan et al. | |

FOREIGN PATENT DOCUMENTS

| | | |
|---|---|---|
| DE | 10312755 A1 | 10/2003 |
| EP | 1103226 | 5/2001 |
| EP | 1205152 A1 | 5/2002 |
| EP | 1254639 A1 | 11/2002 |
| FR | 2726459 | 5/1996 |
| FR | 2749155 | 12/1997 |
| FR | 2844180 | 3/2004 |
| IE | S970323 | 6/1998 |
| JP | 59010807 A | 1/1984 |
| JP | 08252264 | 10/1996 |
| JP | 10082605 A | 3/1998 |
| JP | 10179622 A2 | 7/1998 |
| JP | 2004500953 | 1/2004 |
| WO | WO 95/05783 A1 | 3/1995 |
| WO | WO 96/00049 A1 | 1/1996 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/06939 A1 | 2/2001 |
| WO | WO 01/15638 A1 | 3/2001 |
| WO | WO 01/28442 A1 | 4/2001 |
| WO | WO 01/30248 A1 | 5/2001 |
| WO | WO 01/39678 A1 | 6/2001 |
| WO | WO 01/67972 A2 | 9/2001 |
| WO | WO 01/97721 A2 | 12/2001 |
| WO | WO 02/00270 A1 | 1/2002 |
| WO | WO 02/00275 A1 | 1/2002 |
| WO | WO 02/02024 A1 | 1/2002 |
| WO | WO 02/02158 A1 | 1/2002 |
| WO | WO 02/34150 A2 | 5/2002 |
| WO | WO 02/43603 A1 | 6/2002 |
| WO | WO 02/071960 A1 | 9/2002 |
| WO | WO 02/089712 A1 | 11/2002 |
| WO | WO 03/020143 A1 | 3/2003 |
| WO | WO 03/041618 A2 | 5/2003 |
| WO | WO 03/075805 A1 | 9/2003 |
| WO | WO 03/101350 A1 | 12/2003 |
| WO | WO 2004/071358 A1 | 8/2004 |
| WO | WO 2004/103227 A1 | 12/2004 |
| WO | WO 2004/103228 A1 | 12/2004 |
| WO | WO 2005/009301 A1 | 2/2005 |
| WO | WO 2005/079711 A1 | 9/2005 |

OTHER PUBLICATIONS

Eichholz, K.M. et al. Complications of Revision Spinal Surgery, Neurosurg Focus; (Sep. 15, 2003), 15(3): pp. 1-4.

Farfan, H.F. Effects of Torsion on the Intervertebral Joints. *The Canadian Journal of Surgery* Jul. 1969; 12(3):336-41.

Farfan, H.F. et al. The Relation of Facet Orientation to Intervertebral Disc Failure. *The Canadian Journal of Surgery* Apr. 1967; 10(2):179-85.

Farfan, H.F. The Pathological Anatomy of Degenerative Spondylolisthesis. A Cadaver Study. *Spine.* Sep.-Oct. 1980; 5(5):412-8.

Fosbinder, R.A. et al. Essentials of Radiologic Science. The McGraw-Hill Companies; 2002.

Guyer R. et al. Impliant: Motion Preservation through Total Posterior-Element Replacement. May 7, 2004 Presentation held at Hofburg Center, Vienna, Austria, (2 pages).

Kirkaldy-Willis, W.H. et al. Pathology and Pathogenesis of Lumbar Spondylosis and Stenosis. *Spine.* Dec. 1978; 3(4):319-28.

Kulkarni, et al. Accelerated Spondylotic Changes Adjacent to the Fused Segment Following Central Cervical Corpectomy: Magnetic Resonance Imaging Study Evidence. *J. Neurosurg (Spine I).* 2004; 100: 2-6.

Lam, K. N., et al. X-ray Diagnosis: A Physician's Approach. Springer-Verlag; 1998.

Lombardi, J.S. et al. Treatment of Degenerative Spondylolisthesis. *Spine.* 1985; 10(9): 821-7.

McMillin, C. R. et al. Artificial Spinal Discs with up to Five Years Follow-up. *20th Annual Meeting of the Society for Biomaterials* (Abstract) 1994; p. 89.

Posner, I. et al. A Biomechanical Analysis of the Clinical Stability of the Lumbar and Lumbosacral Spine. *Spine.* 1982; 7(4): 374-389.

Rosenberg, N.J. Degenerative Spondylolisthesis. Predisposing Factors. *The Journal of Bone and Joint Surgery.* 1975; 57-A(4): 467-74.

Slone, R. M. et al. Body CT: A Practical Approach. The McGraw-Hill Companies; 1999.

Stout, G. H. et al. X-Ray Structure Determination: A Practical Guide. 2nd Edition. John Wiley & Sons; 1989.

Szpalski, M., et al. Spine Arthroplasty: A Historical Review. *Eur Spine J.* 2002; 11(Suppl. 2): S65-S84.

UCR Pedicle Screw System from SeaSpine (information available at http://www.seaspine.com/UCR_Pedicle_Screw_System.html). Accessed Dec. 5, 2005.

Victrex of Lancashire, Great Britain. (information on Victrex available at http://www.matweb.com). Accessed Dec. 5, 2005.

Reiley et al; U.S. Appl. No. 11/577,923 entitled "Crossbar spinal prosthesis having a modular design and systems for treating spinal pathologies" filed Apr. 25, 2007.

McLeer, Thomas, U.S. Appl. No. 11/934,724 entitled "Polymeric Joint Complex and Methods of Use" filed Nov. 2, 2007.

McLeer, Thomas, U.S. Appl. No. 11/934,720 entitled "Polymeric Joint Complex and Methods of Use" filed Nov. 2, 2007.

McLeer, Thomas, U.S. Appl. No. 11/934,719 entitled "Polymeric Joint Complex and Methods of Use" filed Nov. 2, 2007.

Reiley, Mark, U.S. Appl. No. 11/934,713 entitled "Facet arthroplasty devices and methods" filed Nov. 2, 2007.

Reiley, Mark, U.S. Appl. No. 11/939,540 entitled "Facet arthroplasty devices and methods" filed Nov. 13, 2007.

Reiley, Mark, U.S. Appl. No. 11/943,458 entitled "Facet arthroplasty devices and methods" filed Nov. 20, 2007.
Reiley, Mark; U.S. Appl. No. 11/949,007 entitled "Facet arthroplasty devices and methods" filed Nov. 30, 2007.
Reiley, Mark, U.S. Appl. No. 11/949,000 entitled "Facet arthroplasty devices and methods" filed Nov. 30, 2007.
Reiley et al.; U.S. Appl. No. 11/948,963 entitled "Prostheses, systems and methods for replacement of natural facet joints with artificial facet joint surfaces" filed Nov. 30, 2007.
Reiley, Mark, U.S. Appl. No. 11/957,208 entitled "Facet arthroplasty devices and methods" filed Dec. 14, 2007.
Reiley et al.; U.S. Appl. No. 11/957,315 entitled "Prostheses, systems and methods for replacement of natural facet joints with artificial facet joint surfaces" filed Dec. 14, 2007.
Reiley, Mark; U.S. Appl. No. 11/957,175 entitled "Facet arthroplasty devices and methods" filed Dec. 14, 2007.
Reiley et al.; U.S. Appl. No. 11/957,290 entitled "Prostheses, systems and methods for replacement of natural facet joints with artificial facet joint surfaces" filed Dec. 14, 2007.
Reiley, Mark; U.S. Appl. No. 11/956,961 entitled "Facet arthroplasty devices and methods" filed Dec. 14, 2007.
Reiley, Mark; U.S. Appl. No. 11/957,149 entitled "Facet arthroplasty devices and methods" filed Dec. 14, 2007.
Reiley, Mark; U.S. Appl. No. 11/957,061 entitled "Facet arthroplasty devices and methods" filed Dec. 14, 2007.
Reiley et al.; U.S. Appl. No. 11/957,259 entitled "Prostheses, systems and methods for replacement of natural facet joints with artificial facet joint surfaces" filed Dec. 14, 2007.
Reiley, Mark; U.S. Appl. No. 12/016,177 entitled "Facet arthroplasty devices and methods" filed Jan. 17, 2008.
Kuiper et al.; U.S. Appl. No. 11/948,994 entitled "Crossbar spinal prosthesis having a modular design and related implantation methods" filed Nov. 30, 2007.
Kuiper et al.; U.S. Appl. No. 11/948,973 entitled "Crossbar spinal prosthesis having a modular design and related implantation methods" filed Nov. 30, 2007.
Kuiper et al.; U.S. Appl. No. 11/957,303 entitled "Crossbar spinal prosthesis having a modular design and related implantation methods" filed Nov. 30, 2007.
McLeer, Thomas; U.S. Appl. No. 11/952,988 entitled "Polymeric joint complex and methods of use" filed Dec. 7, 2007.
Yuan et al.; U.S. Appl. No. 12/027,899 entitled "Prostheses, tools and methods for replacement of natural facet joints with artificial facet joint surfaces," filed Feb. 7, 2008.
Reiley et al; U.S. Appl. No. 12/058,403 entitled "Polyaxial adjustment of facet joint prostheses," filed Mar. 28, 2008.
Goh, JC et al., "Influence of PLIF cage size on lumbar spine stability", Spine, (Jan. 2000), 25(1) Medline abstract (one page).
Head, WC, "Wagner surface replacement arthroplasty of the hip. Analysis of fourteen failures in forty-one hips", J Bone Joint Surg. Am., (Mar. 1981) 63(3), Medline abstract (one page).
Khoo, LT et al., "A biomechanical analysis of the effects of lumbar fusion on the adjacent vertebral motion segment", Proceedings of the 2000 Annual Meeting of the North American Spine Society, New Orleans.
Kotani, Y. et al., "The effects of spinal fixation and destabilization on the biomechanical and histologic properties of spinal ligaments. An in vivo study.", Spine, (Mar. 15, 1998) 23(6), Medline abstract (2 pages).
Lemaire, JP et al., "Intervertebral disc prosthesis: results and prospects for the year 2000", Clinical Orthopaedics and Related Research, No. 337, pp. 64-76.
Nagata, H. et al., "The effects of immobilization of long segments of the spine on the adjacent and distal facet force and lumbrosacral motion", Spine, (Dec. 1993), 18(16):2471-2479, (9 pages).
Nibu, K. et al., "Multidirectional stabilizing potential of BAK interbody spinal fusion system for anterior surgery [see comments]", J Spinal Discord, (Aug. 1997), 10(4), Medline abstract (one page).

Tsantrizos, A. et al., "Segmental stability and compressive strength of posterior lumbar interbody fusion implants", Spine, (Aug. 1, 2000) 25(15), Medline abstract (one page).
Yuan et al; U.S. Appl. No. 11/636,252 entitled "Prostheses, Tools, and Methods for Replacement of Natural Facet Joints with Artificial Facet Joint Surfaces" filed Dec. 8, 2006.
Broman et al; U.S. Appl. No. 11/642,417, entitled "Arthroplasty revision system and method" filed Dec. 20, 2006.
Ohrt et al; U.S. Appl. No. 11/724,927 entitled "Facet and disc arthroplasty system and method" filed Mar. 15, 2007.
Kuiper et al; U.S. Appl. No. 11/635,853, entitled "Crossbar Spinal Prosthesis Having a Modular Design and Related Implantation Methods", filed Dec. 8, 2006.
Reiley et al; U.S. Appl. No. 11/746,027 entitled "Facet Arthroplasty Devices and Methods," filed May 8, 2007.
Reiley et al; U.S. Appl. No. 11/577,872 entitled "Facet Joint Prosthesis" which entered the U.S. from the National Phase Apr. 24, 2007.
Reiley et al; U.S. Appl. No. 11/577,923 entitled "Facet Joint Prostheses" filed Apr. 25, 2007.
Kuiper et al; U.S. Appl. No. 11/577,964 entitled "Crossbar Spinal Prosthesis Having a Modular Design and Systems for Treating Spinal Pathologies," filed Apr. 25, 2007.
Kuiper et al; U.S. Appl. No. 11/577,967 entitled "Crossbar Spinal Prosthesis having a Modular Design and Systems for Treating Spinal Pathologies," filed Apr. 25, 2007.
Reiley, Mark; U.S. Appl. No. 11/750,981 entitled "Facet Arthroplasty Device and Methods," filed May 18, 2007.
Berg, et al; U.S. Appl. No. 11/800,895 entitled "Minimally Invasive Spine Restoration Systems, Devices, Methods, and Kits," filed May 7, 2007.
Gunzberg, R. et al., "Arthroplasty of the Spine". Berlin; New York; Springer, 2004.
Sacher, R. Brochure for presentation at MedTech Insight Conference (Oct. 31, 2003) Boston, MA.
Reiley, Mark; U.S. Appl. No. 11/839,434 entitled "Facet arthroplasty devices and methods", filed Aug. 15, 2007.
Reiley, Mark; U.S. Appl. No. 11/824,012 entitled "Facet arthroplasty device and methods," filed Jun. 29, 2007.
Reiley, Mark: U.S. Appl. No. 11/831,870 entitled "Prostheses systems and methods for replacement of natural facet joints with artificial facet joint surfaces," filed Jul. 31, 2007.
Ralph et al; U.S. Appl. No. 11/837,335 entitled "Angled Washer Polyaxial Connection for Dynamic Spine Prosthesis," filed Aug. 10, 2007.
Reiley, Mark; U.S. Appl. No. 11/775,174 entitled "Facet arthroplasty devices and methods," filed Jul. 9, 2007.
Stone et al; U.S. Appl. No. 11/881,239 entitled "Facet Replacement Device Removal and Revision Systems and Methods" filed Sep. 25, 2007.
Ochoa et al.; U.S. Appl. No. 12/377,546 entitled "Spinal implant," filed Feb. 13, 2009.
Hewko, Brian; U.S. Appl. No. 12/377,552 entitled "Spinal implant," filed Feb. 13, 2009.
Quest et al.; U.S. Appl. No. 12/099,068 entitled "Measurement and trialing system and methods for orthopedic device component selection," filed Apr. 7, 2008.
Reiley, Mark; U.S. Appl. No. 12/176,280 entitled "Facet arthroplasty devices and methods," filed Jul. 18, 2008.
Yuan et al; U.S. Appl. No. 12/163,738 entitled "Prostheses, tools and methods for replacement of natural joints with artificial facet joint surfaces," filed Jun. 27, 2008.
Funk et al; U.S. Appl. No. 12/186,461 entitled "Implantable orthopedic device component selection instrument and methods," filed Aug. 5, 2008.

* cited by examiner

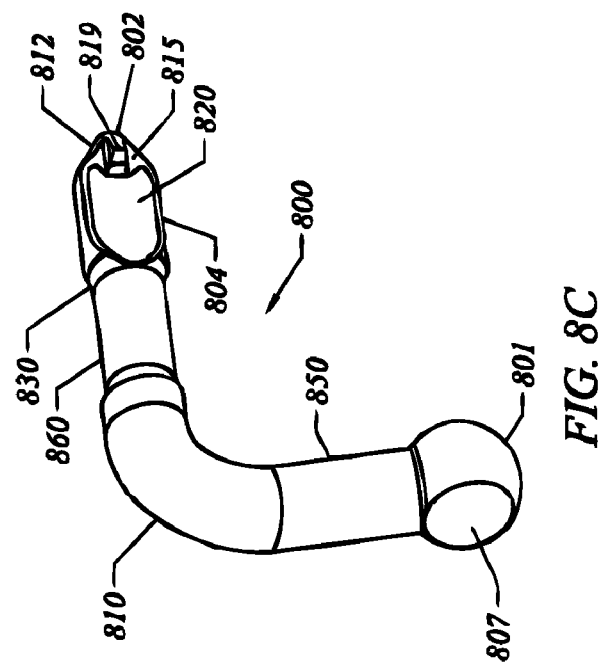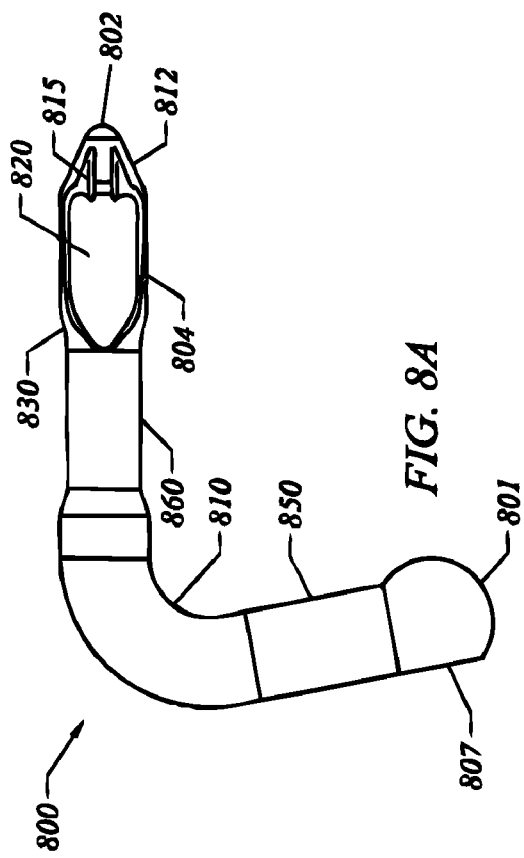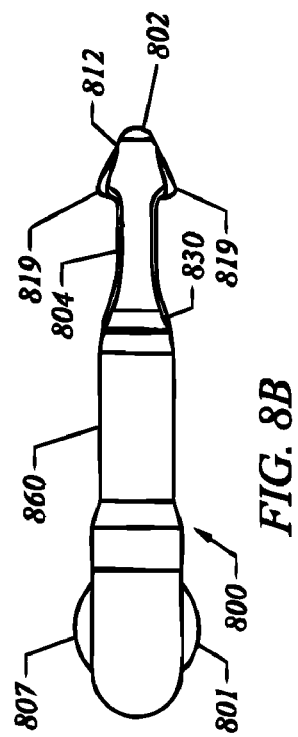

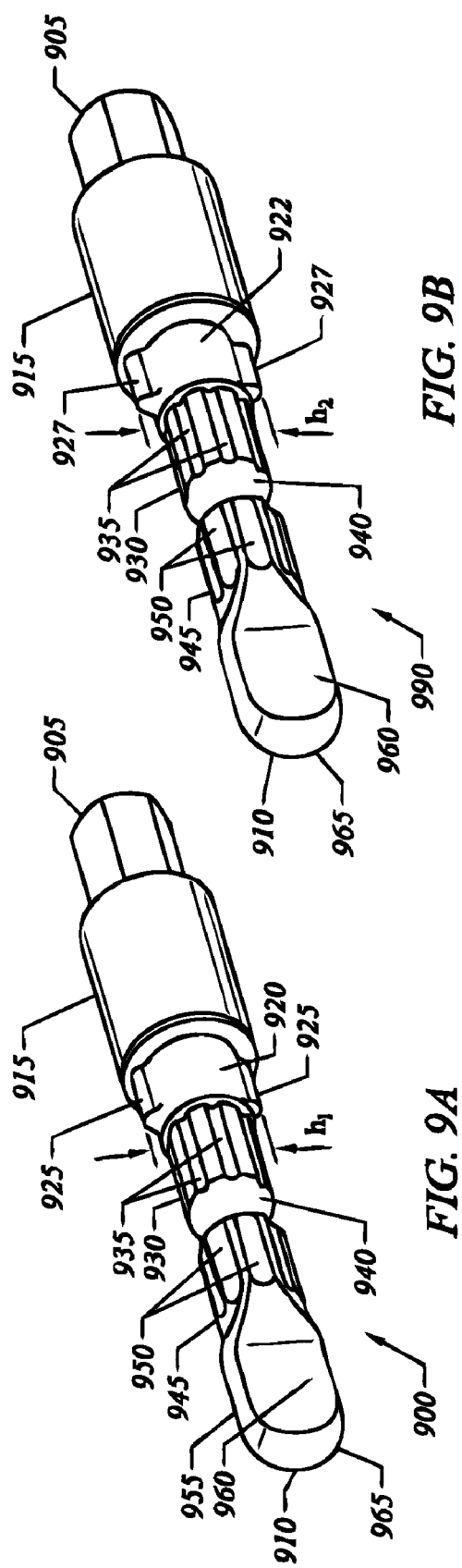

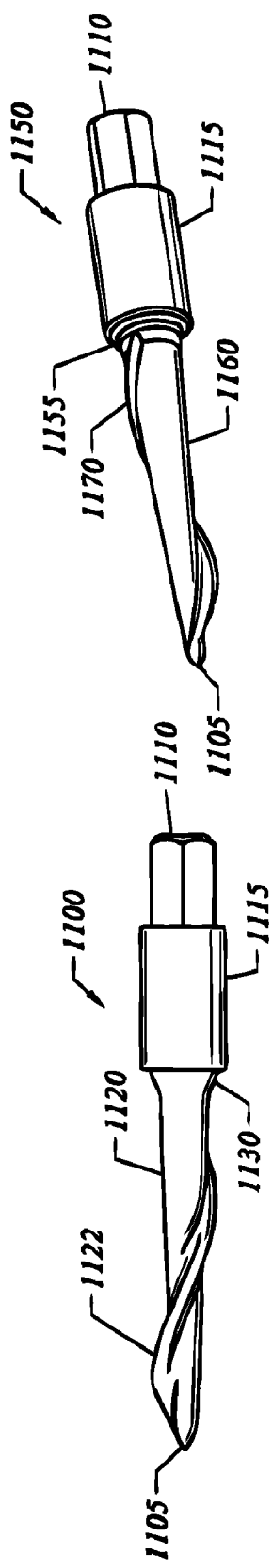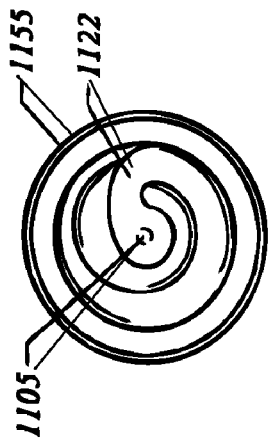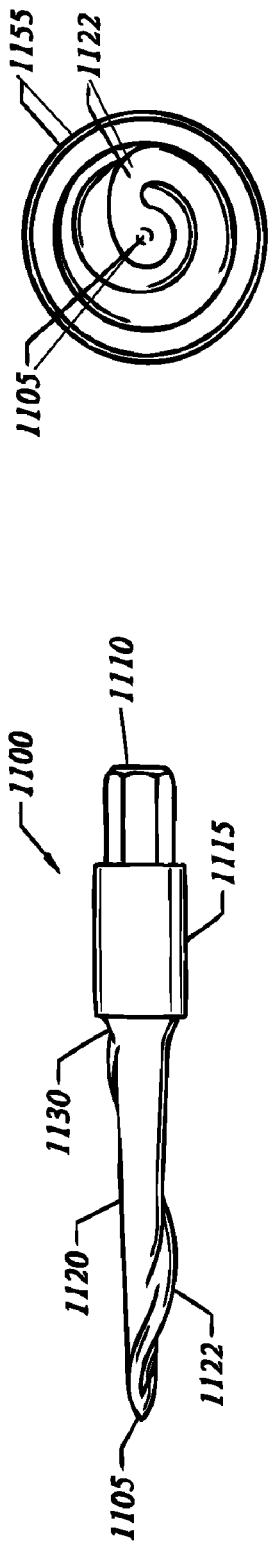
FIG. 11A  FIG. 11B  FIG. 11C  FIG. 11D

ANTI-ROTATION FIXATION ELEMENT FOR SPINAL PROSTHESES

FIELD OF THE INVENTION

This invention relates to prostheses, systems, and methods for treating various types of spinal pathologies, and in particular relates to attachment of prostheses to spinal vertebrae.

BACKGROUND OF THE INVENTION

The human spinal column 10, as shown in FIG. 1, is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five vertebrae, known as S1-S5, while the coccygeal region contains four vertebrae, known as Co1-Co4.

FIG. 2 depicts a superior plan view of a normal human lumbar vertebra 12. Although human lumbar vertebrae vary somewhat according to location, they share many common features. Each vertebra 12 includes a vertebral body 14. Two short bones, the pedicles 16, extend backward from each side of the vertebral body 14 to form a vertebral arch 18.

At the posterior end of each pedicle 16, the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 to the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side of the vertebrae, while the inferior processes 28 are oval plates of bone that jut downward on each side.

The superior and inferior articular processes 26 and 28 each have a natural bony structure known as a facet. The superior articular facet 30 faces upward, while the inferior articular facet 31 (see FIG. 3) faces downward. When adjacent vertebrae 12 are aligned, the facets 30 and 31, capped with a smooth articular cartilage, interlock to form a facet joint 32, also known as a zygapophyseal joint.

The facet joint 32 is composed of a superior half and an inferior half. The superior half is formed by the vertebral level below the joint 32, and the inferior half is formed by the vertebral level above the joint 32. For example, in the L4-L5 facet joint, the superior half of the joint 32 is formed by bony structure on the L5 vertebra (i.e., a superior articular surface and supporting bone 26 on the L5 vertebra), and the inferior half of the joint 32 is formed by bony structure on the L4 vertebra (i.e., an inferior articular surface and supporting bone 28 on the L4 vertebra).

An intervertebral disc 34 between each adjacent vertebrae 12 permits gliding movement between the vertebrae 12. The structure and alignment of the vertebrae 12 thus permit a range of movement of the vertebrae 12 relative to each other.

Back pain, particularly in the "small of the back" or lumbosacral (L4-S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called "pinched" nerves, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods. One method of stabilization is spinal fusion. Another method of stabilization is fixation of any number of vertebrae to stabilize and prevent movement of the vertebrae.

Another type of conventional treatment is decompressive laminectomy. This procedure involves excision of the laminae to relieve compression of nerves.

These traditional treatments are subject to a variety of limitations and varying success rates. None of the described treatments, however, puts the spine in proper alignment or returns the spine to a desired anatomy or biomechanical functionality. In addition, stabilization techniques hold the vertebrae in a fixed position thereby limiting a person's mobility.

Prostheses, systems, and methods exist which can maintain more spinal biomechanical functionality than the above discussed methods and systems and overcome many of the problems and disadvantages associated with traditional treatments for spine pathologies. One example of such prosthesis is shown in FIG. 4. FIG. 4 shows an artificial cephalad and caudal facet joint prostheses 36 and 50 for replacing a natural facet joint. Cephalad joint prosthesis 36 replaces the inferior half of a natural facet joint. Cephalad prosthesis 36 has a bearing element 38 with a bearing surface 40. Caudal joint prosthesis 50 replaces the superior half of a natural facet joint. Caudal prosthesis 50 has a bearing element 52 with a bearing surface 54. Conventional fixation elements 56 attach cephalad and caudal facet joint prostheses 36 and 50 to a vertebra in an orientation and position that places bearing surface 40 in approximately the same location as the natural facet joint surface the prosthesis replaces. The prosthesis may also be placed in a location other than the natural facet joint location.

The spinal column permits the following types of movement: flexion, extension, lateral movement, circumduction and rotation. Each movement type represents relative movement between adjacent vertebra or groups of vertebrae. In addition, these relative movements may be simple movements of a single type but it is more likely that a single movement of the spine may result in several movement types or compound movement occurring contemporaneously. In the illustration of FIG. 4, this translates into movement between the upper vertebral body 12 attached to the cephalad prosthesis 36 and the lower vertebral body 12 attached to caudal prosthesis 50. The movement of the vertebral bodies 12 can result in large, complex forces being generated and transmitted through the prosthesis. The point or points of contact between the bearing surface 40 of the cephalad prosthesis 36 and the bearing surface 54 of the caudal prosthesis 50 can transmit enormous amounts of force onto both the cephalad and caudal facet joint prostheses 36 and 50. The distance between each conventional fixation element 56 and the point or points of contact serves as a lever arm, thereby applying an enormous amount of axial, lateral and torque forces about each of the conventional fixation elements 56, which act as fulcrums. Thus, cephalad prosthesis 36 experiences a force somewhere on bearing surface 40, which is expressed as axial, lateral and torque forces about the conventional fixation element 56 of the cephalad prosthesis 36; and likewise, caudal prosthesis 50 experiences a force somewhere on bearing surface 54, which is expressed as axial, lateral and torque forces about the conventional fixation element 56 of the caudal prosthesis 50. As a result, enormous amounts of such forces can be generated and must be absorbed by the facet joint prostheses and its anchoring system(s).

The existence of enormous amounts of torque presents significant problems for permanent fixation of facet joint prostheses into vertebra. Over time, this torque can act to loosen conventional fixation elements, ruin the facet joint, and require more surgical intervention to restore the facet joint prostheses in the vertebra.

Thus, what is needed is a solution to the torque problem experienced by facet joints of artificial vertebral prostheses.

SUMMARY OF THE INVENTION

The present invention provides prostheses, systems, and methods designed to replace natural facet joints and possibly part of the lamina at virtually all spinal levels including L1-L2, L2-L3, L3-L4, L4-L5, L5-S1, T11-T12, and T12-L1, using attachment mechanisms for securing the prostheses to the vertebrae. The prostheses, systems, and methods help establish a desired anatomy to a spine and return a desired range of mobility to an individual. The prostheses, systems, and methods also help lessen or alleviate spinal pain by relieving the source nerve compression or impingement.

For the sake of description herein, the prostheses that embody features of the invention are identified as either "cephalad" or "caudal" with relation to the portion of a given natural facet joint they replace. As previously described, a natural facet joint, such as facet joint 32 (FIG. 3), has a superior half and an inferior half. In anatomical terms, the superior half of the joint is formed by the vertebral level below the joint, which can thus be called the "caudal" portion of the facet joint because it is closer to the feet of the person. The inferior half of the facet joint is formed by the vertebral level above the joint, which can thus be called the "cephalad" portion of the facet joint because it is closer to the head of the person. Thus, a prosthesis that, in use, replaces the caudal portion of a natural facet joint (i.e., the superior half) will be called a "caudal" prosthesis. Likewise, a prosthesis that, in use, replaces the cephalad portion of a natural facet joint (i.e., the inferior half) will be called a "cephalad" prosthesis.

In one aspect, a vertebral prosthesis includes a first bearing element and a first fixation element coupled to the first bearing element. The first bearing element can be shaped to form a facet joint with a second bearing element. The first fixation element can be inserted into a hole in a vertebra.

The first fixation element can include an anti-rotation element. The anti-rotation element can be coupled to at least a portion of the vertebra. This portion of the vertebra can define the hole in the vertebra. The anti-rotation element can be adapted to resist a rotational force. With no resistance, the rotational force may cause rotation of the first fixation element within the hole in the vertebra.

In some embodiments, the hole in the vertebra may be just one hole. In other embodiments, there may be multiple holes in the vertebra. In the case of multiple holes in the vertebra, the first fixation element can be inserted into just one hole in the vertebra, or into multiple holes in the vertebra. Also in the case of multiple holes in the vertebra, the rotation force may cause rotation of the first fixation element within just one hole in the vertebra, or within multiple holes in the vertebra.

In various embodiments, the second bearing element with which the first bearing element forms a facet joint, can be part of a second prosthesis, or part of a natural vertebra. If the second bearing element is part of a second prosthesis, the second prosthesis can be one of the embodiments discussed herein, or another type of prosthesis.

The fixation element may be secured directly into the vertebral body, or can be attached and/or "fixed" using a supplemental fixation material such as bone cement, allograft tissue, autograft tissue, adhesives, osteo-conductive materials, osteo-inductive materials and/or bone scaffolding materials. In one embodiment, the first fixation element can be enhanced with a bony in-growth surface, such as surfaces created using sintering processes or chemical etching (Tecomet Corporation of Woburn, Mass.) which can help fix the fixation element within a vertebra. The bony in-growth surface can cover a portion or all of the first fixation element.

A width of the prosthesis may be constant, or vary. For example, a width of a proximal end of the first fixation element can exceed a width of a distal end of the first fixation element. A width of a proximal end of the anti-rotation element can exceed a width of a distal end of the anti-rotation element. In an alternate embodiment, a width of a distal end of the first fixation element can exceed a width of a proximal end of the first fixation element.

The anti-rotation element can be coupled to the vertebra by being directly connected to the vertebra. The anti-rotation element also can be coupled with at least cement to the vertebra.

In some embodiments, the anti-rotation element includes a wing. The wing can be positioned at a proximal of distal portion of the first fixation element. When the first fixation element is inserted into a first hole or holes in the vertebra, the wing can be inserted into a second hole of the vertebra.

In some embodiments, the anti-rotation element includes a blade. The blade can be positioned at a proximal or distal portion of the first fixation element. When the first fixation element is inserted into a first hole or holes in the vertebra, the blade can also be inserted into the first hole in the vertebra.

In some embodiments, the anti-rotation element includes a paddle. The paddles can be positioned at a distal or proximal portion of the first fixation element. The first fixation element can be straight, or include one or more bends. The anti-rotation element can include one or more grooves positioned distally and/or proximally from the paddle. The anti-rotation element can also include other features, such as one or more wings positioned proximally or distally from the paddle, and/or one or more blades positioned proximally or distally from the paddle.

In some embodiments, the anti-rotation element includes an intersection of three or more projections. The intersection can be positioned at a distal or proximal portion of the first fixation element.

In some embodiments, the anti-rotation element includes a helical projection. The anti-rotation element can include an intersection of two or more helical projections.

In some embodiments, the anti-rotation element includes a longitudinal depression. The longitudinal depression can have a longitudinally varying profile. The longitudinal depressions can be a helical longitudinal depression, a groove, or a flute. The longitudinal depression can help define a spline. The anti-rotation element may further include a perimeter (circumferential) depression. The perimeter depression can be a perimeter undercut.

In some embodiments, the anti-rotation element can include separated members. The first fixation element can include a longitudinal hole. A filling element can be inserted into the longitudinal hole and spread the separated members of the anti-rotation element. The separated members can be positioned at a distal portion of the first fixation element.

In various embodiments, the anti-rotation element can define a hole, into which the first fixation element is inserted. Alternatively, the first fixation element can define a hole into which the anti-rotation element is inserted. In various embodiments, the hole can be tapered (using, for example, a tapered broach) and/or the first fixation element can have a taper. The anti-rotation element can have a taper. The anti-rotation element can be coupled to the first fixation element by an interference fit. The anti-rotation element can include a bend, or be straight. The first fixation element can be straight, or include a bend.

In some embodiments, the anti-rotation element includes one or more proximal projections.

In another aspect, a vertebral prosthesis includes a first bearing element and a first fixation element. The first bearing element can be shaped to form a facet joint with a second bearing element. The first fixation element can be coupled to the first bearing element. The first fixation element can be inserted into a hole in the vertebra. The first fixation element can be shaped to resist a rotational force. With no resistance, the rotational force may cause rotation of the first fixation element within the hole in the vertebra.

In various embodiments, the second bearing element with which the first bearing element forms a facet joint, can be part of a second prosthesis, or part of a natural vertebra. If the second bearing element is part of a second prosthesis, the second prosthesis can be one of the embodiments discussed herein, or another type of prosthesis.

The first fixation element can be enhanced with a bony in-growth surface, which can help fix the fixation element within a vertebra. The bony in-growth surface can cover a portion or the entire first fixation element.

A width of the prosthesis may be constant, or vary. For example, a width of a proximal end of the first fixation element can exceed a width of a distal end of the first fixation element. A width of a proximal end of the anti-rotation element can exceed a width of a distal end of the anti-rotation element. In another embodiment, the width of a distal end of the anti-rotation element can exceed a width of a proximal end of the anti-rotation element.

The anti-rotation element can be coupled to the vertebra by being directly connected to the vertebra. The anti-rotation element also can be coupled with at least cement to the vertebra.

In some embodiments, the first fixation element can be shaped with a bend. The first fixation element can have a taper.

In another aspect, a vertebral prosthesis method includes coupling a first bearing element to a first fixation element, coupling an anti-rotation element to the first fixation element (as a feature of the component or as a separate component), and inserting the first fixation element into a hole in the vertebra. The first bearing element can be shaped to form a facet joint with a second bearing element. The anti-rotation element can be adapted to resist a rotational force. With no resistance, the rotational force may cause rotation of the first fixation element within the hole in the vertebra.

In another aspect, a vertebral prosthesis preparation method includes perforating a vertebra with at least a first hole, supporting a perforation guide with a guide support, guiding a perforation tool with the perforation guide, and perforating the vertebra with a second hole (or shaped cavity) aligned by the perforation guide. The first hole can be shaped to receive a prosthetic fixation element. The guide support can be positioned by a portion of the vertebra defining a hole. The second hole can be shaped to receive a first prosthetic anti-rotation element.

In some embodiments, the method can include the step of using the perforation tool while at least partly removing the guide support.

Various embodiments include the step of perforating the vertebra with a third hole aligned by the perforation guide. The third hole can be shaped to receive a second prosthetic anti-rotation element.

In some embodiments, the method can include the step of using the perforation tool while least partly removing the guide support.

The guide support can be inserted while perforating the vertebra with the first hole. The guide support can be inserted after perforating the vertebra with the first hole.

In yet another aspect, a vertebral prosthesis tool includes a guide support and a perforation guide.

The guide support can be stabilized by a first hole of the vertebra. The first hole can be shaped to receive a prosthetic fixation element of the vertebral prosthesis. The vertebral prosthesis can form a facet joint with a second vertebral prosthesis.

The perforation guide can be coupled to the guide support. The perforation guide can guide a perforation tool to perforate the vertebra with a second hole aligned by the perforation guide. The second hole can be shaped to receive a prosthetic anti-rotation element of the vertebral prosthesis.

Other features and advantages of the invention are set forth in the following description and drawings, as well as in the appended claims.

BRIEF DESCRIPTION OF THE DRAWINGS

FIGS. 8A, 8B, and 8C provide a side elevation view, plan view, and perspective view, respectively, of a vertebral prosthesis portion with a fixation element having a bend, a paddle, and additional distally located anti-rotation elements;

FIGS. 9A and 9B provide a perspective views of a vertebral prosthesis portion with a paddle, straight fixation element, and additional anti-rotation elements;

FIGS. 11A, 11B, 11C, and 11D provide a side view, a perspective view, another side view, and a distal end view, respectively, of a vertebral prosthesis portion with a helical projection;

DETAILED DESCRIPTION OF THE PREFERRED EMBODIMENT

Although the disclosure presented herein provides details to enable those skilled in the art to practice various embodiments of the invention, the physical embodiments disclosed herein merely exemplify the invention, which may be embodied in other specific structure. Accordingly, while preferred embodiments of the invention are described below, details of the preferred embodiments may be altered without departing from the invention. All embodiments that fall within the meaning and scope of the appended claims, and equivalents thereto, are intended to be embraced by the claims.

Embodiments of the present invention may be used, with advantage, on a wide variety of prosthesis devices, particularly spinal prostheses. Some of these prostheses, systems, and methods are discussed in the following applications entitled: "Facet Arthroplasty Devices And Methods", by Mark A. Reiley, Ser. No. 09/693,272, filed Oct. 20, 2000, now U.S. Pat. No. 6,610,091, issued Aug. 26, 2003; "Prostheses, Tools And Methods For Replacement Of Natural Facet Joints With Artificial Facet Joint", by Lawrence Jones et al., Ser. No. 10/438,295, filed May 14, 2003; "Prostheses, Tools And Methods for Replacement Of Natural Facet Joints With Artificial Facet Joint", by Lawrence Jones et al., Ser. No. 10/438, 294, filed May 14, 2003; "Prostheses, Tools And Methods For Replacement Of Natural Facet Joints With Artificial Facet Joint", by Lawrence Jones et al., Ser. No. 10/615,417, filed Jul. 8, 2003; "Prosthesis For the Replacement of a Posterior Element of a Vertebrae", by T. Wade Fallin et al., U.S. Pat. No. 6,419,703; "Multiple Facet Joint Replacement", by E. Marlowe Goble et al., U.S. Pat. No. 6,565,605; "Facet Joint Replacement"; by E. Marlowe Goble et al., U.S. Pat. No. 6,579,319; "Method and Apparatus for Spine Joint Replacement"; by E. Marlowe Goble et al., Ser. No. 10/090,293, filed Mar. 4, 2002; and "Polyaxial Adjustment Of Facet Joint Prostheses, by "Mark A. Reiley et al., Ser. No. 10/737,705, filed Dec. 15, 2003, all of which are hereby incorporated by reference for all purposes.

Figure 1:
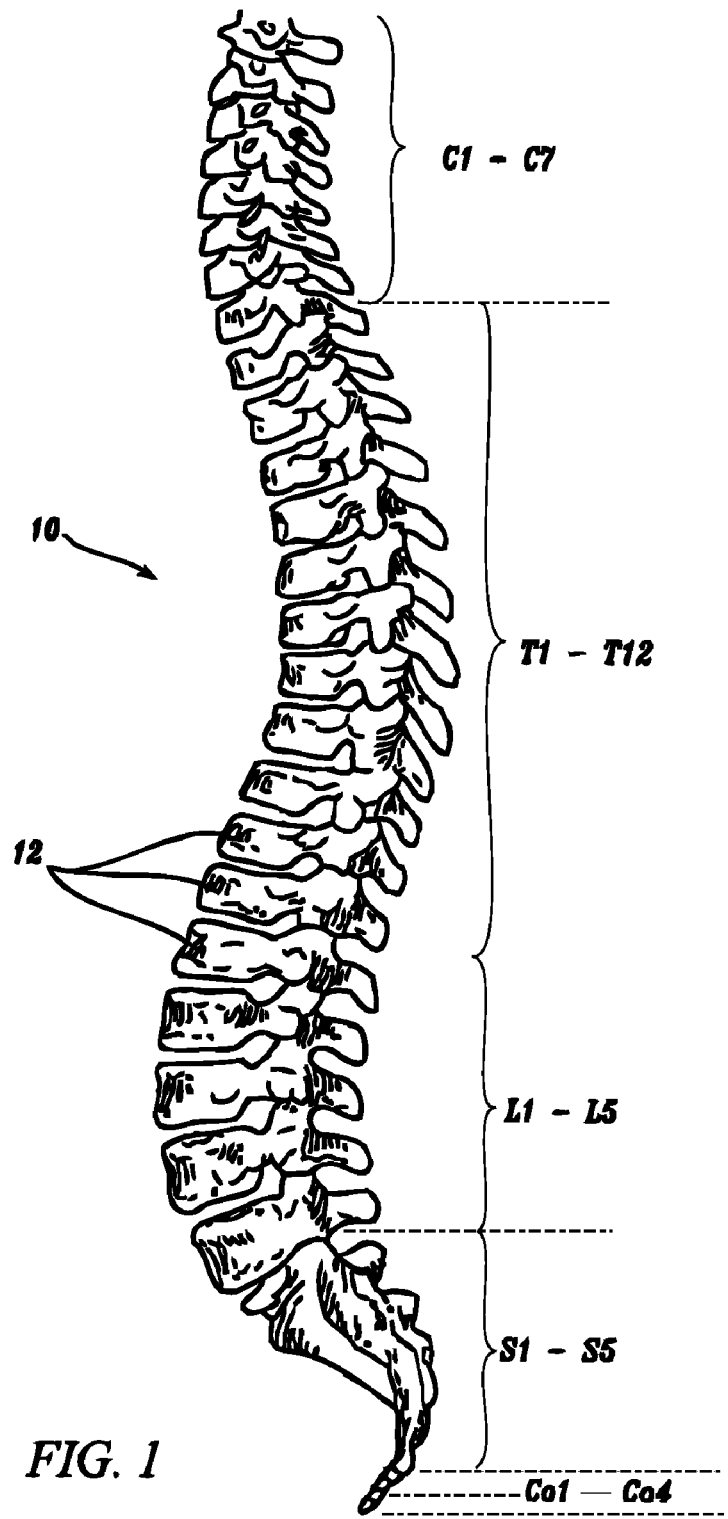
FIG. 1 is a lateral elevation view of a normal human spinal column.
Figure 2:
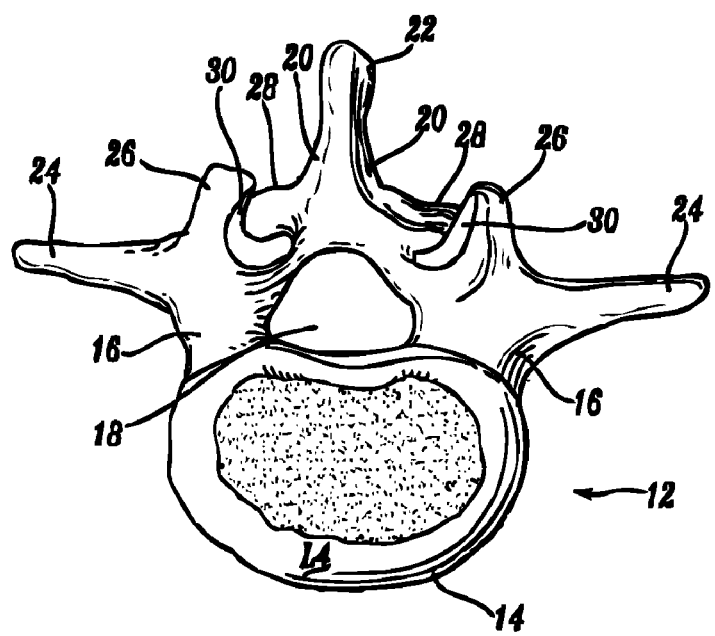
FIG. 2 is a superior plan view of a normal human lumbar vertebra.
Figure 3:
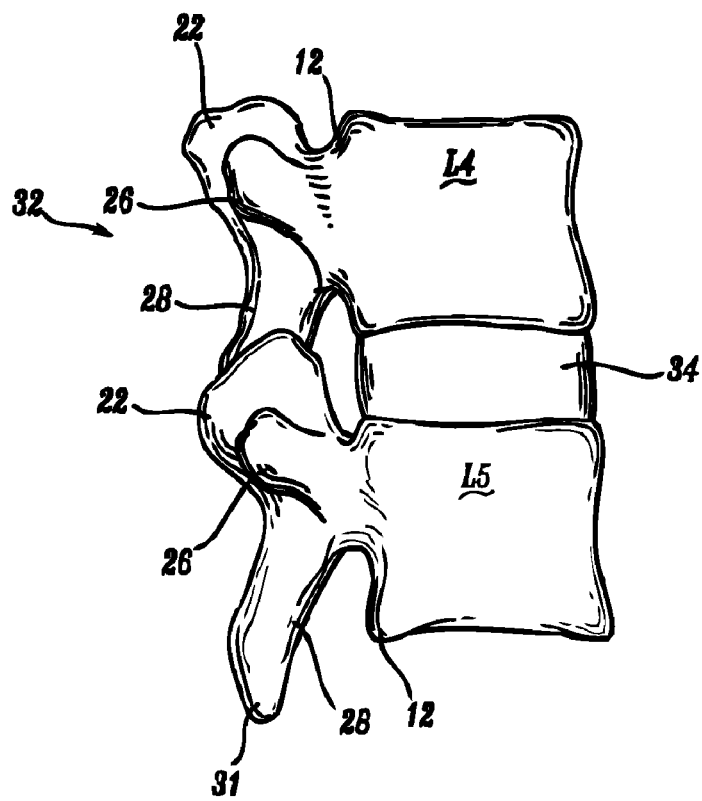
FIG. 3 is a lateral elevation view of adjoining normal human lumbar vertebrae L4 and L5.
Figure 4:
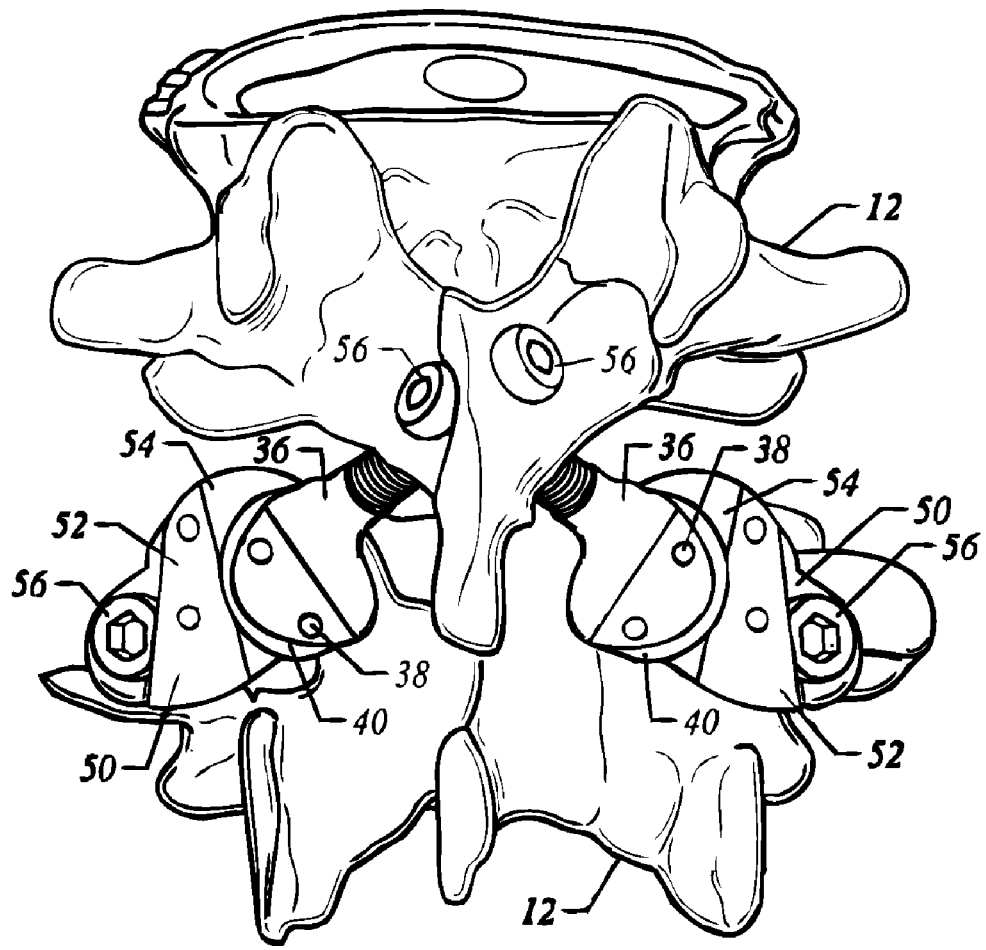
FIG. 4 is a perspective view of a cephalad prosthesis for replacing the inferior half of a natural facet joint on a superior vertebral body.
Figure 5A:
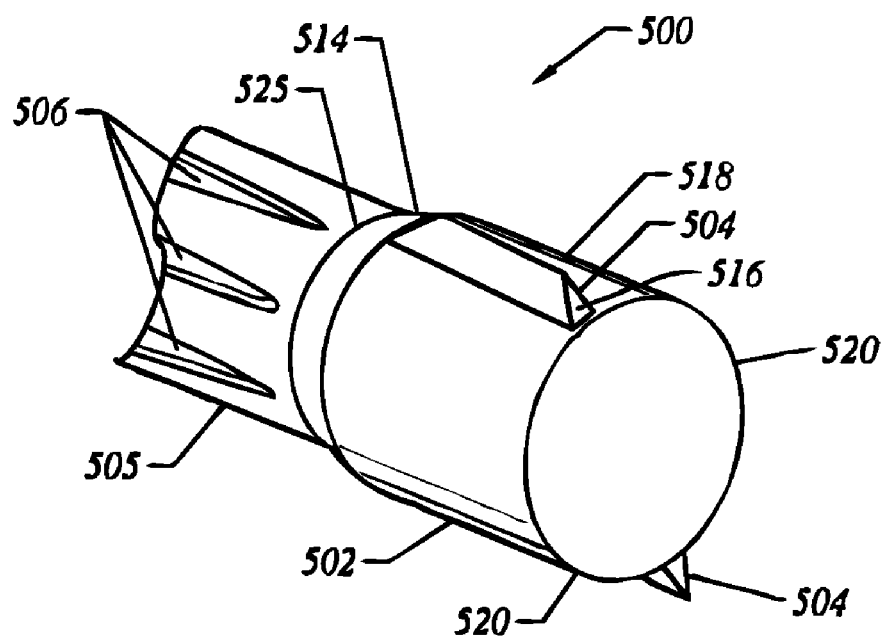
FIGS. 5A and 5B provide a perspective and proximal sectional view, respectively, of a vertebral prosthesis portion with blades.
Figure 5B:
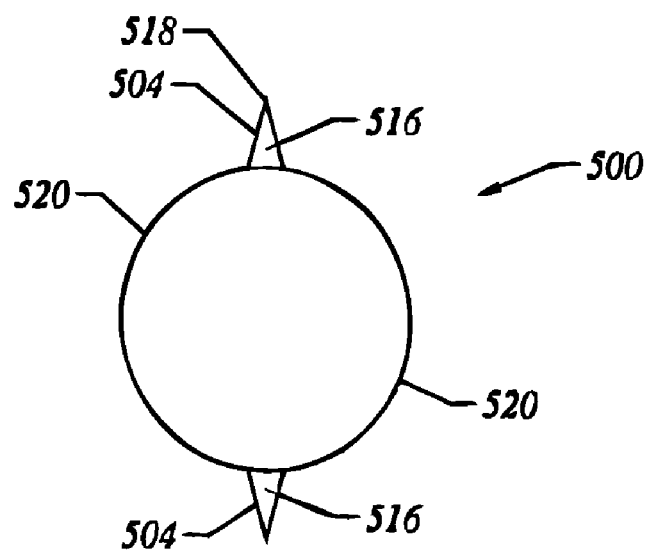

FIGS. 5A and 5B show one embodiment of a vertebral prosthesis portion 500 with proximally positioned blades 504 that function as anti-rotation elements. The vertebral prosthesis portion 500 has a proximal portion 502 with a pair of blades 504. The two blades 504 are positioned on opposite sides of the perimeter of the vertebral prosthesis portion 500, and are thus positioned apart by about 180 degrees. Also shown is a grooved portion 505 having grooves 506 along the periphery of the vertebral prosthesis portion 500. The illustrated grooved portion 505 has grooves 506 that taper in a proximal direction along the vertebral prosthesis portion 500. Other groove configurations as possible, for example, see FIGS. 6A, 6B, 6C, and 9A and 9B discussed in further detail below. Additionally, there may be embodiments having no grooves. In the illustrated embodiment, a transition section 525 separates the proximal portion 502 from the grooved portion 505. While the illustrated transition section 525 has a uniform, linear transition from the diameter of the proximal portion 502 to the grooved portion 505, other transition sections are possible depending upon the relative geometry of the grooved portion 505 and the proximal portion 502. In one embodiment, the transition section 525 can serve as a cement restrictor, preventing and/or inhibiting cement flow out of the vertebral body. In some embodiments, a transition section 525 may not be used.

Figure 15C:
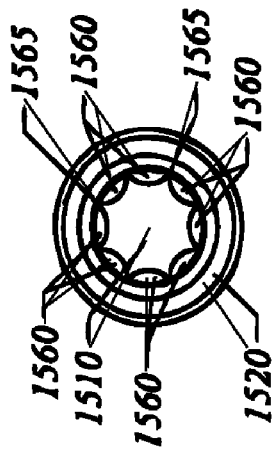
FIGS. 15A, 15B, 15C, and 15D provide, a side view, an isometric view and a distal end view, a sectional view taken along the line shown in the distal end view FIG. 15C respectively, of a vertebral prosthesis portion with tapered longitudinal depressions and perimeter depressions.
Figure 15D:
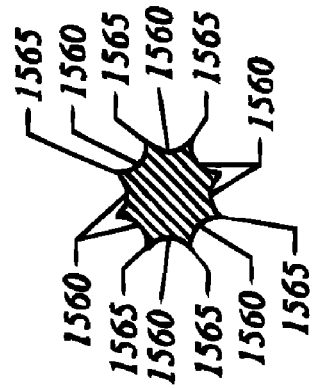
Figure 15A:
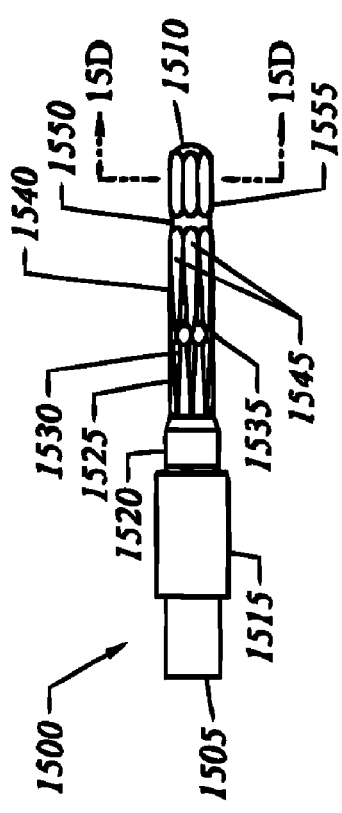

Alternative embodiments of the vertebral prosthesis portion 500 may have one blade, three blades, or more blades. Alternative embodiments can also employ a different amount of spacing other than 180 degrees between multiple blades for embodiments with multiple blades, and the spacing can be the same or different between the multiple blades. While the embodiment illustrated in FIGS. 5A and 5B illustrates blades 504 separated by convex portions 520, other configurations are possible. For example, the blades 504 may be separated by concave sections as illustrated, for example, in FIG. 15D or in combinations of convex and concave portions. Although the illustrated blades 504 have pointed triangular profiles, alternative embodiments can have rounded points, no points, and/ or other profiles of other geometries, such as square, rectangular, trapezoidal, arcuate, etc and combinations thereof. In addition, blades 504 have a uniform incline section 514 and decline section 516 and a single height ridge 518. Other configurations are possible. For example, the incline and decline sections 514, 516 may be different as in, for example, FIGS. 17A, 17B and 17C. In one embodiment, the blades 504 are sufficiently small such that the blades 504 can fit into the same vertebral hole that receives the fixation element. It is to be appreciated that embodiments of the proximal anti-rotation elements of vertebral prosthesis portion 500 may be used in combination with other vertebral prosthesis portions described below. In addition, the advantages of the proximal anti-rotation features of vertebral prosthesis portion 500 may be combined with conventional prosthesis fasteners resulting in a hybrid prosthesis fastener having a conventional distal portion and a proximal portion having anti-rotations feature or features of the vertebral prosthesis portion 500.

Figure 6C:
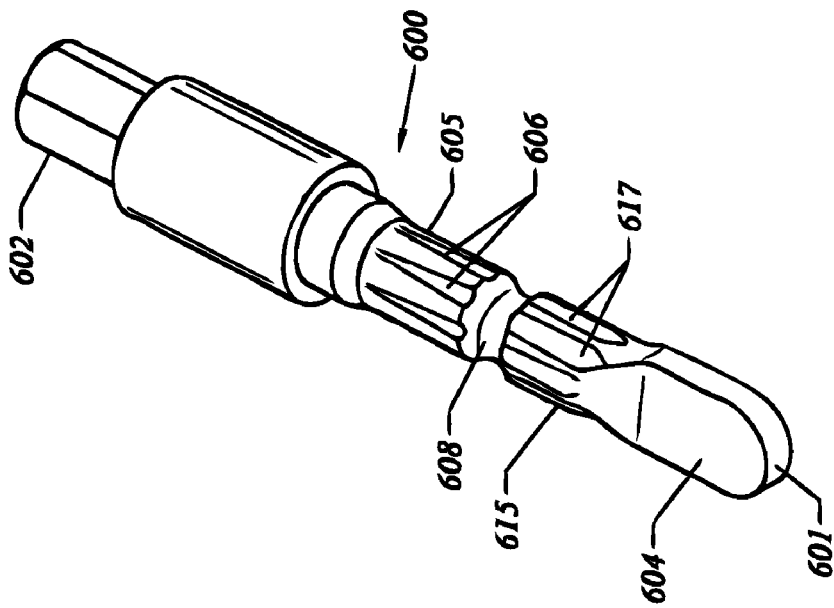
FIGS. 6A, 6B, and 6C provide a side elevation view, another side elevation view, and a perspective view, respectively, of a vertebral prosthesis portion with a paddle.
Figure 6B:
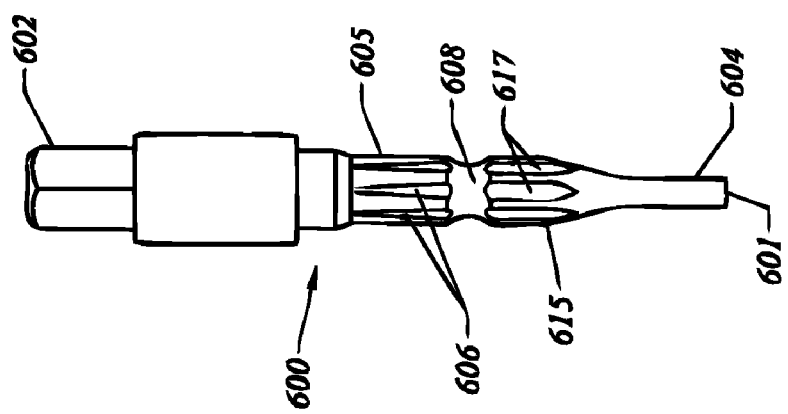
Figure 6A:
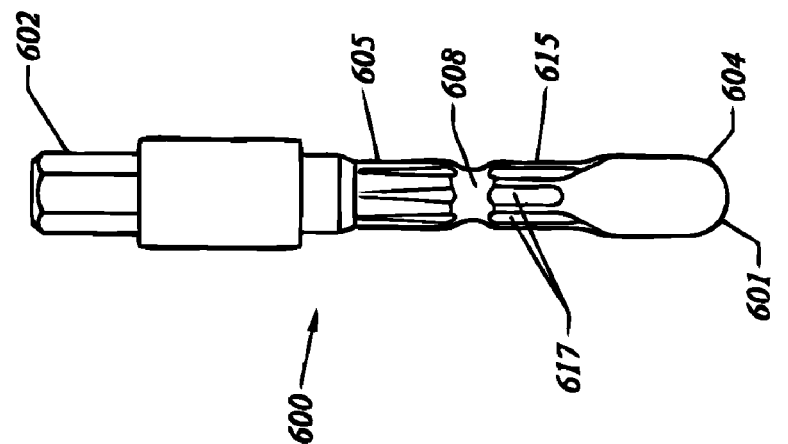
Figure 7C:
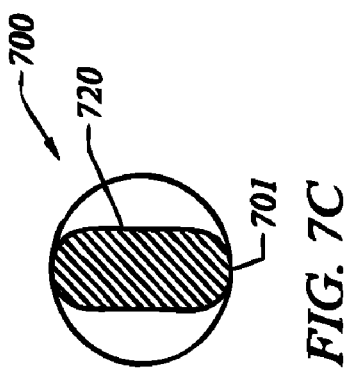
FIGS. 7A, 7B, 7C, and 7D provide a side elevation view, plan view, distal sectional view, and perspective view, respectively, of a vertebral prosthesis portion with a fixation element having a bend and a paddle.
Figure 7D:
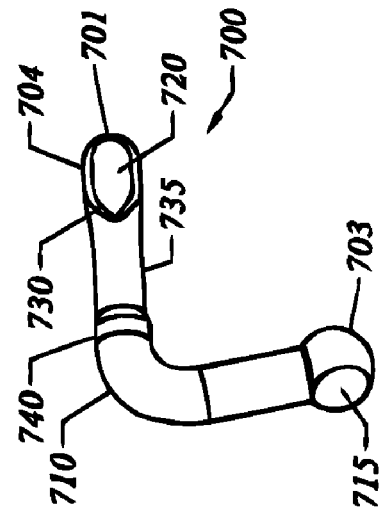
Figure 7A:
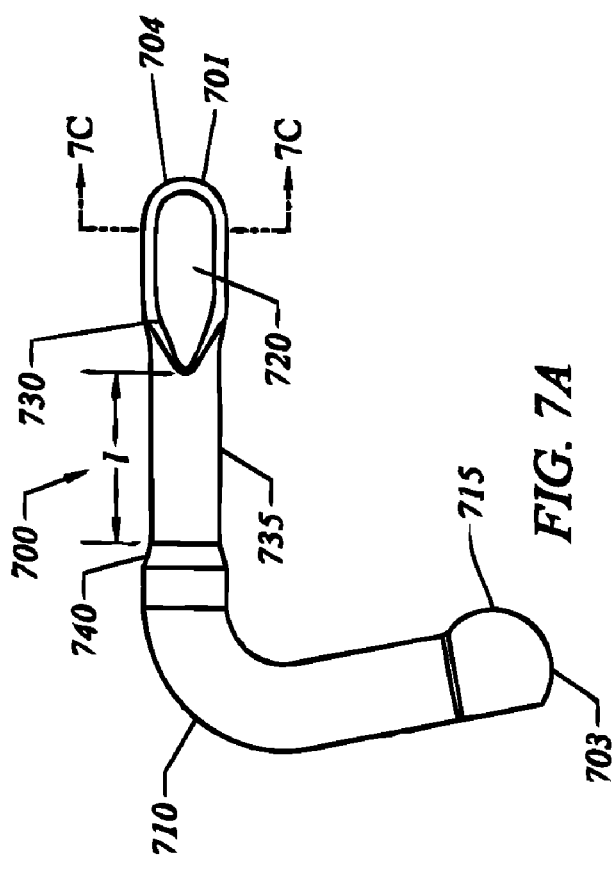
Figure 7B:
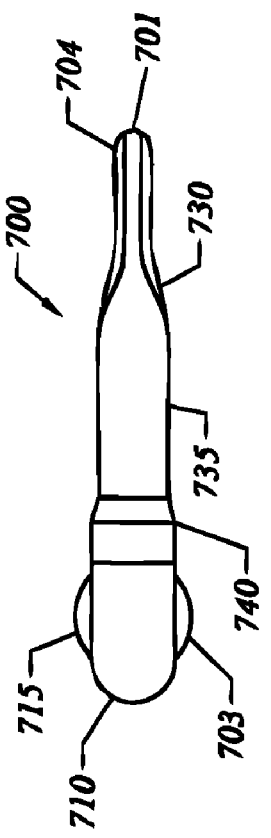

FIGS. 6A, 6B, and 6C show an embodiment of a vertebral prosthesis portion 600 with a paddle 604 and grooves as an anti-rotation element. While desiring not to be bound by theory, it is believed that the wide surface area(s) provided by the anti-rotational paddle embodiments of the present invention provide greater resistance to the torque loads applied to the prosthesis and attempted rotation of the paddle within the vertebra. For example, the additional of surface projections and/or pits can significantly increase the total surface are of the prosthesis, thereby increasing the ability of any adhesion between the prosthesis and the surrounding material (such as bone cement, epoxy or in-growing bony material) to secure the prosthesis in position. As another example, the additional of surface projections and pits can interact with the surrounding material to create a geometric or mechanical "interlock" that resists relative motion between the prosthesis and the surrounding material. As such, the paddle embodiments of the present invention described herein act as improved anti-rotational elements. Similarly, other anti-rotation elements described herein are also used to counteract the torque loads developed within and acting upon various portions of vertebral prosthesis.

The vertebral prosthesis portion 600 has a distal end 601 and a proximal end 602. The proximal end 602 is configured to accept tooling and instruments to secure the vertebral prosthesis portion 600 into the vertebra and/or to provide an attachment point to another vertebral prosthesis component. A distal portion of a fixation element has a paddle 604 configured to act as an anti-rotation element to prevent the rotation of the vertebral prosthesis portion 600 once implanted into a vertebra. Alternative embodiments of the vertebral prosthesis portion 600 can have multiple paddles. Although the illustrated paddle 604 has a rounded profile, alternative embodiments may have different profiles including, for example, one or more corners. Although the illustrated paddle 604 is flat, alternative embodiments can have nonflat contours, with one or more concave and/or convex features.

Figure 15B:
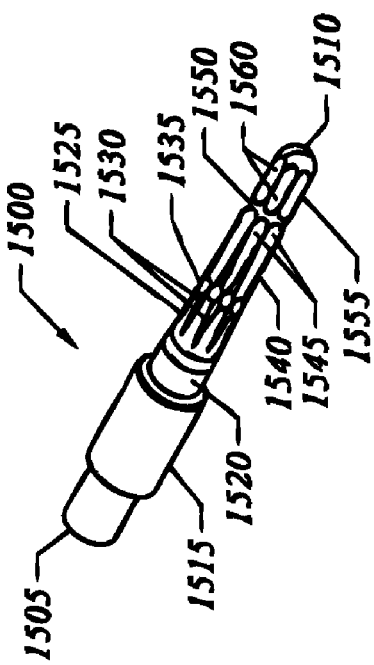

FIGS. 6A, 6B, and 6C also illustrate an embodiment of an anti-pull out feature of the vertebral prosthesis portion 600. Embodiments of the vertebral prosthesis portion 600 also include anti-pull out features. As used herein, an anti-pull out feature refers to an element or combination of elements of a prosthesis portion or fastener acting to mitigate, minimize or counteract forces bearing upon the prosthesis portion or fastener to disengage, loosen, advance, pull or otherwise axially translate the fastener relative to a desired position on or within the vertebra. (For purposes of this disclosure, anti-pullout forces can be interpreted to include, but are not limited to, both "pull" and "push" forces which serve to translate the prosthesis along a longitudinal axis outward or inward relative to the targeted vertebral body.) In the illustrated embodiment, the vertebral prosthesis portion 600 includes a proximal grooved portion 605 having proximal grooves 606 and a distal grooved portion 615 having distal grooves 617. In the illustrated embodiment, proximal grooves 606 have a proximal tip with a width that increases distally and distal grooves 617 have a nearly constant width terminating in a distal tip. A reduced diameter portion 608 separates the proximal grooved portion 605 from the distal grooved portion 615. The proximal grooves 606, distal grooves 617 and reduced diameter section 608 act to increase the surface area of the vertebral prosthesis portion 600. By increasing the surface area of the vertebral prosthesis portion 600 provides greater attachment between the vertebral prosthesis portion 600 and the vertebra. The greater amount of surface area may be used advantageously with bone cement, bone growth compounds or other materials used to bond the external surfaces the vertebral prosthesis portion 600 to the interior of the vertebra. The greater surface area allows, in embodiments where bone fixation cement is used, more cement to be present along the length and a particularly greater amount of cement or fixation material to be present about the reduced diameter section 608. The increased amount of cement present adjacent the reduced diameter portion 608 produces a section of increased diameter that counteracts pull out forces. Other configurations, arrangements and geometries of the proximal grooved portion 605, reduced diameter portion 608, and distal grooved portion 615 are possible. For example, different groove configurations are possible (e.g., FIGS. 9A, 13A and 15F), there may be multiple distal or proximate grooved portions (e.g., FIG. 15B), multiple reduced diameter portions (e.g., FIG. 15B) or different paddle configurations (e.g., FIGS. 7A-7D and FIGS. 8A-8C).

FIGS. 7A, 7B, 7C, and 7D show an embodiment of a vertebral prosthesis portion 700 with a fixation element having a bend 710, and a paddle 704 as an anti-rotation element, similar to the vertebral prosthesis portion shown in FIGS. 6A, 6B, and 6C. The vertebral prosthesis portion 700 includes a distal end 701 and a proximal end 703. The proximal end 703 includes a bearing element 715 for engagement to other portions of the vertebral prosthesis. To accommodate a number of different facet joint prosthesis configurations, the fixation element includes a bend 710 connected to a shaft 735 having a paddle 704 attached thereto.

The vertebral prosthesis portion 700 also illustrates an embodiment of a modular prosthesis fastener concept. For example, in some embodiments, the shaft 735 is detachably fastened to the attachment point 740. The shaft 735 has a length "l" between the attachment point 740 and the proximate end of the paddle 704. The shaft 735 is detachably coupled to the attachment point 740 to allow for shafts 735 of different lengths to be used with different configurations of the vertebral prosthesis portion 700 thereby providing a modular vertebral prosthesis. As such, in use, the shaft 735 may be detached from the attachment point 740 and replaced with a shaft 735 having a different length "l" as needed until the proper alignment of the vertebral prosthesis is achieved. Modular components can be attached to the prosthesis using one or more attachments methods well known in the art, including threaded screws, morse tapers, adhesives or set screws.

While the modular concept has been described with regard to the vertebral prosthesis 700, it is to be appreciated that other embodiments of the vertebral prosthesis portions described herein may have a portion or portions that are detachably coupled in furtherance of the modular vertebral prosthesis concept. For an alternative example, the shaft 735 may be of fixed length and permanently attached to the attachment point 740 while the detachable attachment point is positioned between the shaft 735 and the paddle 704 thereby allowing paddles 704 of different lengths to be used. In yet another alternative, both the shaft and the paddle may have detachable attachment points thereby allowing various shaft lengths and configurations and paddle lengths and configurations to be used in furtherance of the modular vertebral prosthesis concepts described herein. It is to be appreciated that the detachable attachment point may be positioned between any portion or portions of the embodiments of the vertebral prosthesis portions described herein and elsewhere in this patent application.

In an alternate embodiment, one or more sections of the vertebral prosthesis may be made of a deformable or shape-memory material (such as Nitinol or similar materials), which permits the physician to make adjustments to the prosthesis geometry to "form-fit" the implant to the patient's specific anatomy. In the case of Nitinol, the material can be heated or cooled away from the body temperature (depending upon the type of material and it's martensitic/austenitic properties), be deformed to a desired shaped, and then held in the deformed position and allowed to return to the body temperature, thereby "hardening" into the desired shape or form. Such an embodiment would facilitate a reduction in the number of sections or "modules" required for a modular prosthesis, as each module could assume a variety of desired positions.

While the angle of the illustrated bend 710 is acute, other embodiments of the vertebral prosthesis portion 700 can have bend 710 having a right angle or an obtuse angle. Alternative embodiments of the vertebral prosthesis portion 700 may include two, three, or more bends 710. In the illustrated embodiment, the paddle 704 has a flat surface 720 and a proximal end having a transition portion 730. The flat surface 720 is illustrated in the same plane in which the fixation element has the bend 710. In other embodiments, the paddle 704 has a flat surface 720 in another plane, and/or a nonflat contour, with one or more concave and/or convex features or have paddle shapes similar to the distal portions illustrated in FIGS. 10A, 10B, 13A and 13B. The transition portion 730 has a width that decreases linearly in a proximal direction. Other configurations of the transition portion 730 are possible for transitioning from the paddle 704 to the shaft 735 of the vertebral prosthesis portion 700. The alternative shapes of the transition portion include, for example, a non-linear decreasing proximal width, asymmetric portions, curved portions or compound portions.

FIGS. 8A, 8B, and 8C show an embodiment of a vertebral prosthesis portion 800 with a fixation element having a bend 810, and compound anti-rotational elements included in the paddle 804. A proximal socket element 807 is attached to the bend 810 by a proximal shaft 850. A distal shaft 860 couples the bend 810 to the paddle 804. While the illustrated bend 810 has only a single, acute angle, it is to be appreciated that in other embodiments the bend 810 may have a have a right angle or an obtuse angle and may include two, three, or more bends. Further to the modular and configurable vertebral prosthesis concepts described herein, one or more detachable connections may exist between the various elements of the vertebral prosthesis portion 800. In addition, elements of different lengths (e.g., shafts 850, 860), size (e.g., socket 807 and paddle 804) or angular orientation (e.g., bend 810, paddle 804) may be advantageously employed in furtherance of the modular vertebral prosthesis concept.

Embodiments of the vertebral prosthesis portion 800 may have paddle 804 embodiments similar to the paddle embodiments shown and described with regard to vertebral prosthesis portion 700 (see e.g., FIGS. 7A, 7B, 7C, and 7D). The paddle 804 may include a flat face similar to face 720 described above, however, other configurations are possible. As illustrated, paddle 804 has a non-flat face 820 that may be convex, concave or have portions that are combinations of convex, concave or flat. Alternatively, the paddle surface 820 may be a flat surface in another plane, and/or a nonflat contour, with one or more concave and/or convex features. As illustrated, the paddle surface 820 is in the same plane in as the bend 810. In other embodiments, the paddle surface(s) 820 may not be in plane with the bend 810.

In addition to having paddle surfaces 820 of varying shape than earlier described paddle embodiments, embodiments of the paddle 804 also include compound or more than one anti-rotation elements. As discussed above, the paddle surfaces generally provide an anti-rotation or rotation-resistant component to the vertebral prosthesis. Additionally, embodiments of paddle 804 include other anti-rotational elements such as the enlarged distal tip 812 having grooves 815 and projections 819. The enlarged distal tip 812 may have one or more grooves 815 positioned distally from the paddle 804. In some embodiments, the grooves occur in the same plane as the plane of the paddle 804. In other embodiments, grooves can occur in multiple planes and/or planes that are different from the plane of the paddle 804. Similarly, the distal tip may have projections 819 in the same or different plane with the faces of paddle 804. While the illustrated projections 819 appear identical in shape and size and are arranged parallel to the axis of the proximal shaft 860, it is to be appreciated that the projections 819 may have different configurations. The projections 819 may not all be the same size or have the same overall shape, have an asymmetrical orientation relative to the paddle 804 or be positioned in a non-parallel arrangement with regard to the axis of the proximal shaft 860.

FIGS. 9A and 9B illustrate an alternative embodiment of a vertebral prosthesis portion having anti-rotation and anti-pullout elements. The paddle 955 and proximal ridges 925, 927 act as anti-rotation elements. The reduced diameter section 940, grooved sections 930, 945 and reduced shank diameter 920, 922 act as anti-pullout elements. The vertebral prosthesis portions 900 and 990 are similar in many regards to vertebral prosthesis portion 600 if FIGS. 6A, 6B and 6C. However, several differences are important. Paddle 955 has a flat face 960 but a rounded, tapered distal end 965 instead of a flat distal edge found on paddle 604 (see FIG. 6B). Proximal grooves 935 have a constant width instead of a tapered width (see FIG. 6A grooves 606). Distal grooves 950 have a uniform width and a rounded distal end instead of a distal tip (grooves 617 of FIG. 6B).

One notable difference between the prosthesis potions 900, 990 and the prosthesis portion 600 is the addition of the proximal anti-rotation sections 920, 922. The proximal anti-rotation sections 920, 922 include a shank having a diameter less than the shank 915 and a plurality (two in the illustrated embodiments) of ridges that act as proximal anti-rotation elements. Vertebral prosthesis portion 900 has a proximal anti-rotation portion 920 and ridges 925 having an overall height $h_1$. Vertebral prosthesis portion 990 has a proximal anti-rotation portion 922 and ridges 927 having an overall height $h_2$ These embodiments advantageously provide reduced shank sizes thereby allowing for increased cement mantle (if cement is desired), while still providing a mechanical "interlock" with the surrounding tissue that resists prosthesis rotation (In various embodiments, the ridges can desirably engage surrounding cortical bone at the pedicle entry point, which is often stronger than the cancellous bone contained within the vertebral body, although the ridges' engagement with either or both types of bone will serve to resist rotation to varying degrees). In a specific embodiment of the prosthesis portion 900 the height $h_1$ is 8.25 mm and the proximal anti-rotation section diameter is 6.5 mm but still maintains a moment of inertia ($I_y$) equal to that of a 7 mm rod. In a specific embodiment if the prosthesis portion 990, the overall ridge height $h_2$ is 8.75 mm and the proximal anti-rotation section diameter is 6.0 mm but the embodiment still maintains a moment of inertia ($I_y$) equal to that of a 7 mm rod.

It is to be appreciated that the vertebral prosthesis portions 900 and 990 may differ from the illustrated embodiments. For example, there may be one or more ridges present in the proximal anti-rotation sections (as opposed to the pair of ridges disclosed above). The additional ridges need not have uniform cross sections or be uniformly spaced about the perimeter of the proximal anti-rotation section. The paddle face 960 may have a different face such as convex, concave or other compound shape or combinations thereof.

Figure 10A:
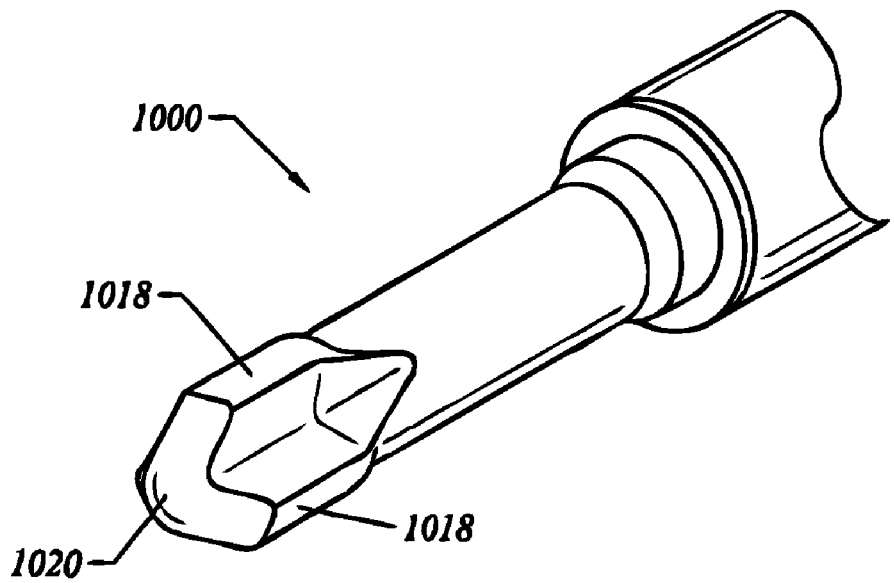
FIGS. 10A and 10B provide a perspective view and a distal end view, respectively, of a vertebral prosthesis portion with an intersection of multiple projections.
Figure 10B:
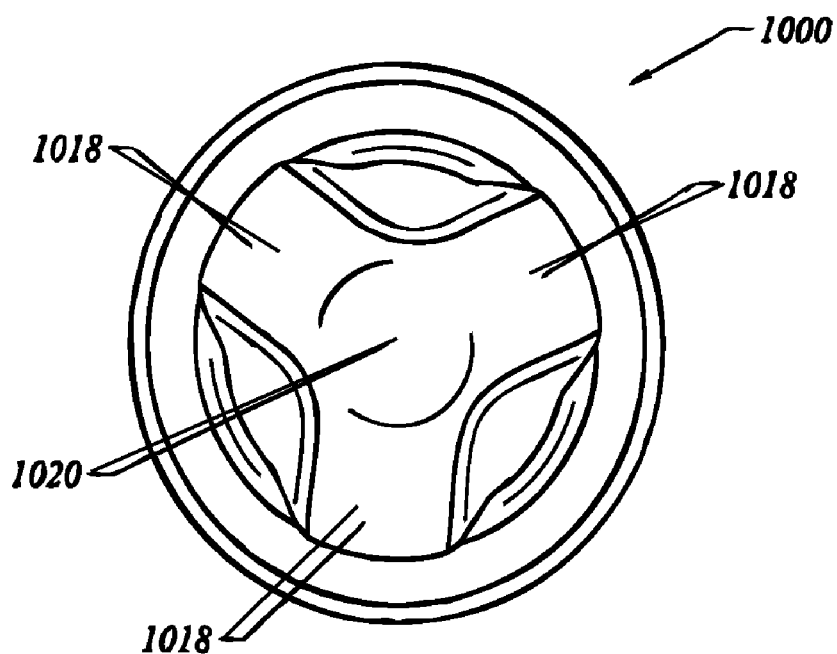

FIGS. 10A and 10B show an embodiment of a vertebral prosthesis portion 1000 with an intersection of multiple projections as an anti-rotation element. The distal portion of the fixation element has three projections 1018. The three projections 1018 meet at an intersection 1020 of the projections. The three projections 1018 meet at the center, as viewed from the distal end. In alternative embodiments multiple projections can meet at an off-center position as viewed from the distal end. The three projections 1018 are positioned equidistantly about the perimeter of the fixation element, and are thus positioned apart by about 120 degrees. Alternative embodiments can have one projection, two projections, four projections, or more projections. Alternative embodiments can also employ a different amount of spacing other than 120 degrees between multiple projections, and the spacing can be the same or different between the multiple projections. Although the illustrated projections 1018 have a trapezoidal profile as viewed from the side of the prosthesis portion, alternative embodiments can have other profiles of other geometries, such as square, rectangular, triangular, etc.

FIGS. 11A, 11B, 11C and 11D illustrate another embodiment of a vertebrae prosthesis portion having a helical projection that acts as an anti-rotation element. FIGS. 11A, 11B are right and left side views of a vertebral prosthesis portion 1100. The vertebral prosthesis portion 1100 has a distal tip 1105 and a proximal fitting 1110. The proximal fitting 1110 is attached to a shank 1115 and a tapered shaft 1120. A single step transition section 1130 is used to change diameters from the shank 1115 to the proximal end of the tapered shaft 1120. A rounded profile ridge 1122 spirals proximally from the distal tip 1105 to the transition section 1130. While the illustrated embodiment shows the ridge 1122 beginning at the distant tip 1105 and spiraling continuously to the transition section 1130, other configurations are possible where, for example, the ridge begins at a position proximate to the distal tip 1105 or ends distal to the transition section 1130. Moreover, the ridge 1122 need not be continuous but may be segmented into a plurality of sections have the same or different lengths. (If desired, the interrupted ridge could additionally act as a "self-locking" feature to resist undesired removal of the prosthesis.) The ridge 1122 need not be of uniform height but may have various heights that increase or decrease in a proximal direction or alternate such as in a sinusoidal pattern. FIG. 11C illustrates a view of the vertebral prosthesis 1100 viewed proximally from the distal tip 1105. The ridge 1122 has a pitch of about one revolution meaning that as the ridge 1122 spirals along the tapered shaft 1120 it traces a path that traverses a single rotation absent the tapered shaft. In alternative embodiments, the ridge 1122 may traverse the tapered shaft 1122 at an increased pitch (more than one revolution) or a decreased pitch (less than one revolution, see e.g. FIG. 11D). In addition to changing the pitch, the ridge 1122 may have other cross-sectioned shapes other than rounded such as, for example, a sharp edge or triangular cross section as in FIG. 11D.

Vertebral prosthesis portion 1150 illustrates and alternative embodiment of the helical ridge anti-rotation element (FIG. 11D). Vertebral prosthesis portion 1150 is similar in many respects to vertebral prosthesis portion 1100 and similar reference numbers have been used for like components. Vertebral prosthesis portion 1150 has a multiple step transition section 1155 between the shank 1115 and the tapered shaft 1160. The tapered shaft 1160 has a more gradual taper than the taper in tapered shaft 1120. The ridge 1170 has a sharp edge and a pitch of less than one revolution. Desirably, the transition in the shaft will reduce and/or eliminate the stress concentration or "stress riser" inherent in the diameter transition.

Figure 12A:
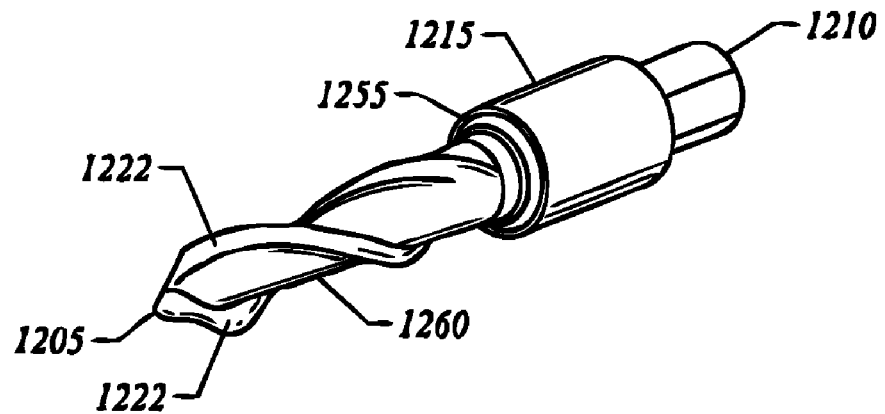
FIGS. 12A and 12B provide a perspective view and a distal end view, respectively, of a vertebral prosthesis portion with two helical projections.
Figure 12B:
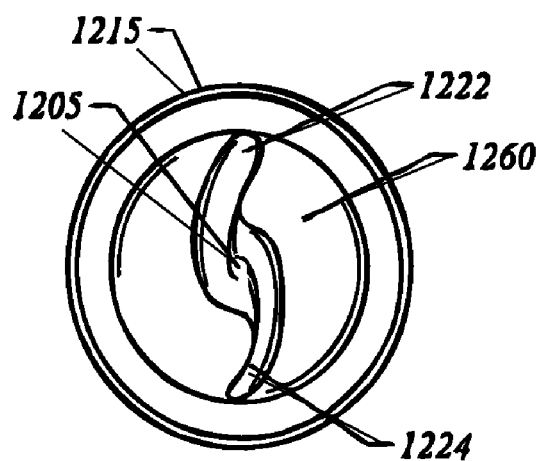

In an alternative embodiment to the single ridge anti-rotation element (FIGS. 11A-11D), a vertebral prosthesis portion 1200 may have more than one ridge anti-rotation element (FIGS. 12A, 12B). The vertebral prosthesis portion 1200 has a distal tip 1205 and a proximal end 1210. A shank 1215 is attached to the proximal end 1210 and a stepped transition section 1255. A tapered shaft 1260 extends from the stepped transition section 1255 to the distal tip 1205. Two ridges 1222, 1224 project outwardly from the tapered shaft 1260. Using the orientation at the distal tip 1205 (FIG. 12B), the upper ridge 1222 has a rounded top surface and is wider than the lower ridge 1224 that is narrower with a more pronounced or sharper ridge top surface. In the illustrated embodiment, ridges 1222, 1224 have the same pitch of less than one revolution. It is to be appreciated that the ridges 1222, 1224 could have a pitch greater than one or each ridge could have a different pitch or more than two ridges could traverse tapered shaft 1260. Other alternative ridge configurations as described above with regard to ridges 1122 and 1170 (e.g., FIGS. 11A, 11D) are applicable to ridges 1222, 1224. The ridges 1222, 1224 project from opposite sides of the tapered shaft 1260 and are evenly spaced apart by a separation angle of about 180 degrees. Alternative embodiments can have three ridge or helical projections, four helical projections, or more helical projections. Alternative embodiments and the illustrated embodiment may also employ a separation angle or angles of other than 180 degrees between helical projections and the spacing can be uniform between all projections or be variable and/or different between projections. As described above, the ridges or helical projections may begin at a location on the tapered shaft 1260 proximal to the distal tip 1205 and may end distal to the stepped transition section 1255.

Figure 13A:
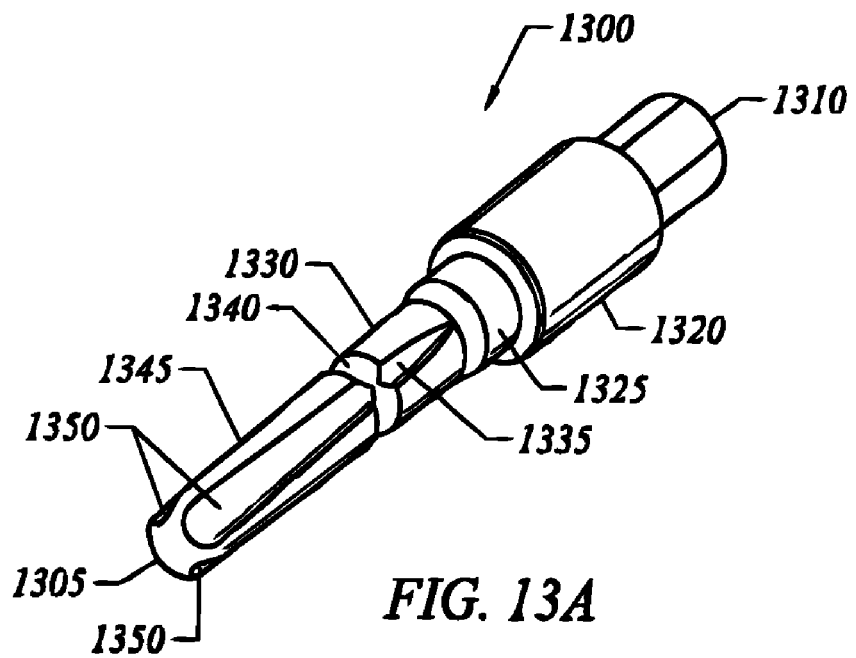
FIGS. 13A and 13B provide a perspective view and a distal end view, respectively, of a vertebral prosthesis portion with longitudinal depressions.
Figure 13B:
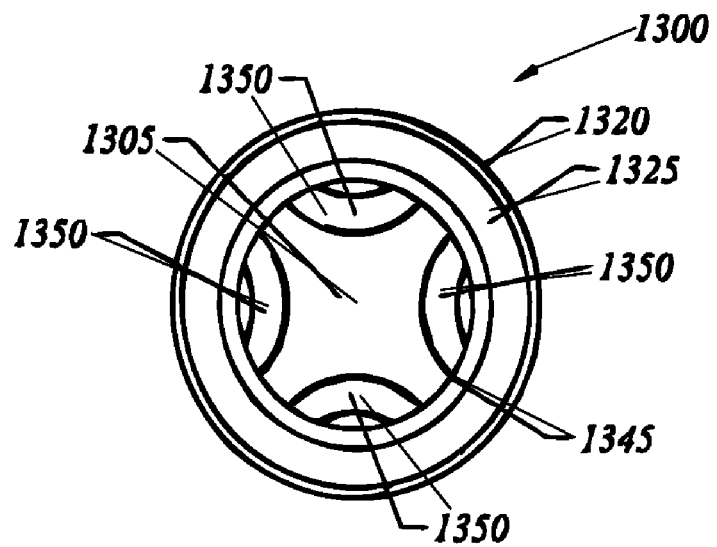

FIGS. 13A and 13B illustrate an embodiment of a vertebral prosthesis portion 1300 have longitudinal grooves as anti-rotation elements. The vertebral prosthesis portion 1300 has a distal end 1305 and a proximate end 1310 attached to a shank 1320. A transition section 1325 separates the shank 1320 from the proximal grooved section 1330 having grooves 1335 formed therein. A reduced diameter section 1340 separates the proximal grooved section 1330 from the distal grooved section 1345. The distal grooved section 1345 has grooves 1350 formed therein. As can be seen more clearly in distal end view of FIG. 13B, there are four grooves 1350 in the illustrated embodiment. The groove configuration of vertebral prosthesis portion 1300 differs from earlier described grooves 506 (FIG. 5A), grooves 945, grooves 935 (FIGS. 9A, 9B) in a number of ways. The grooves 1350 are much wider and there are fewer of them than in previous embodiments. The grooves 1350 are wider distally and taper proximally to the reduced diameter section 1340. The grooves 1350 are evenly spaced about the distal grooved section 1345 and have the same rounded cross section (see FIG. 13B). However, in alternative embodiments, the grooves 1350 have different spacings and different cross-sectioned shapes.

It is to be appreciated that each of the longitudinal grooves or depressions 1350 has a longitudinally varying profile, narrowing as the groove extends proximally. In alternative embodiments, the longitudinally varying profile can widen or remain constant as the longitudinal depression or groove extends proximally (if desired, they can change in depth as they narrow in width). Although in the illustrated embodiment, all of the longitudinal depressions or grooves 1350 are identical, in other embodiments, the multiple longitudinal depressions can differ, for example by having different profiles, lengths, starting and/or ending points, etc. Alternative embodiments can have one longitudinal depression, two longitudinal depressions, three longitudinal depressions, five longitudinal depressions, or more longitudinal depressions. Alternative embodiments can also employ a different amount of spacing other than 90 degrees between multiple longitudinal depressions for embodiments with multiple longitudinal depressions, and the spacing can be the same or different between the longitudinal depressions.

The proximal grooved section 1330 has fewer grooves 1335 than previously described proximal grooved sections (e.g. FIGS. 5A, 9A and 9B). There are two grooves 1335 in the proximal grooved section 1330, although only one is visible in FIG. 13A. Grooves 1335 align with a distal groove 1350 in the illustrated embodiment. The grooves 1335 have a groove profile that is wider distally and tapering proximally to a tip at transition section 1325. It is to be appreciated that alternative embodiments may have one or more grooves 1335 to align one for one with grooves 1350. In another alternative embodiment, there may be the same number of grooves 1335 as grooves 1350 however, grooves 1335 may be offset radically so as not to align axially with grooves 1350 as illustrated. Both grooves 1350, 1335 need not be parallel to the longitudinal axis if the vertebral prosthesis portion 1300 but may instead be arranged in non-parallel configurations with respect to the longitudinal axis of the vertebral prosthesis portion 1300.

Figure 14A:
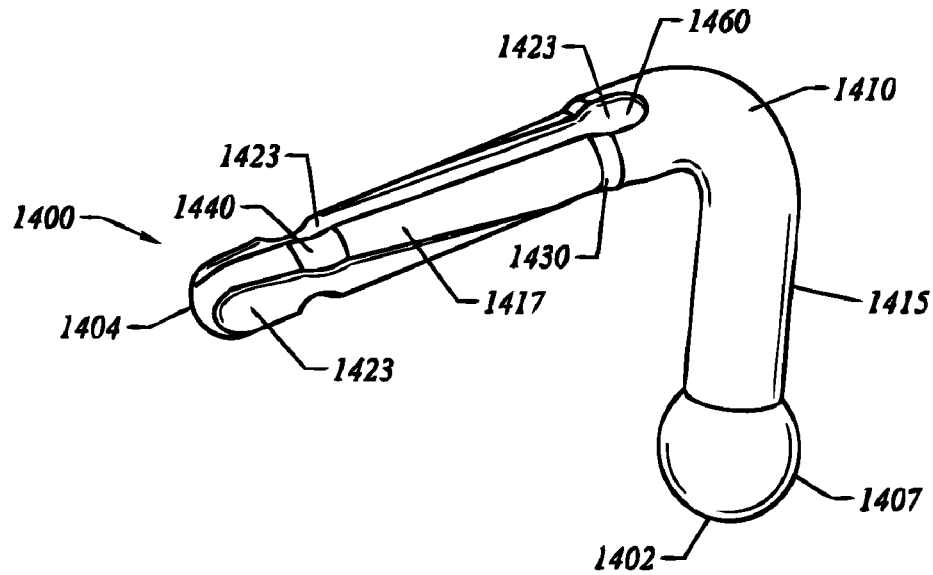
FIGS. 14A and 14B provide a perspective view and a distal end view, respectively, of a vertebral prosthesis portion with helical longitudinal depressions and a fixation element with a bend.
Figure 14B:
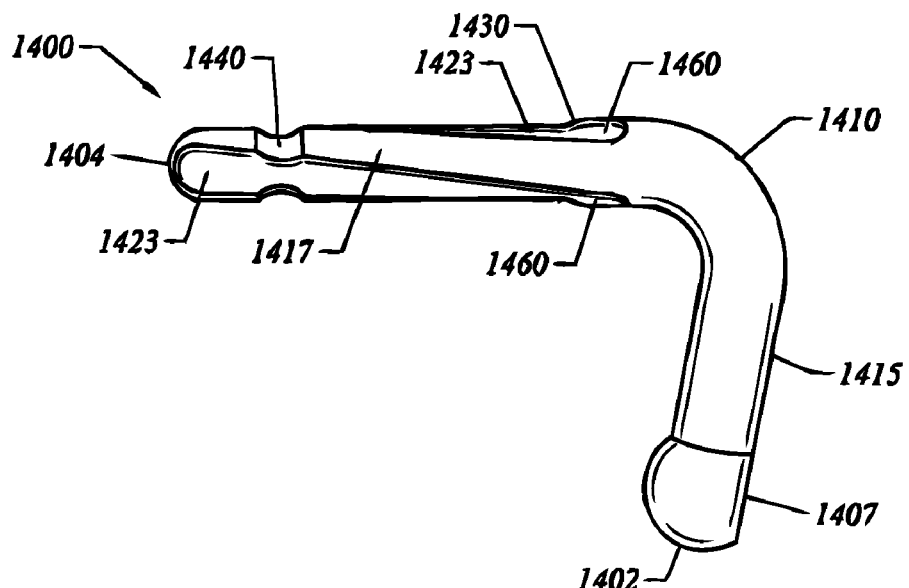

FIGS. 14A and 14B show an embodiment of a vertebral prosthesis portion 1400 with helical longitudinal depressions as anti-rotation elements and a fixation element with a bend. The illustrated embodiment of the vertebral prosthesis portion 1400 has a distal tip 1404 and a proximal end 1402. The proximal end 1402 includes a socket element 1407 for further attachment to a vertebral prosthesis. (Alternatively, the element 1407 could comprise a bearing surface for slidably engaging a corresponding bearing surface (not shown) of a caudal portion of a vertebral prosthesis). Proximal shaft 1415 is attached to the socket element 1407 and the bend 1410. The tapered section 1430 transitions from the proximal shaft 1415 to the distal shaft 1417 [as the proximal shaft 1415 is a different diameter than the distal shaft 1417.] Other transitions are possible such as a stepped transition (e.g. section 740 of FIG. 7B) or no transition if the diameter of the shafts 1415 and 1417 are the same.

The distal shaft 1417 includes a plurality of longitudinal depressions 1423 extending from the distal end 1404 to a point beyond the tapered section 1430. The proximal end of the longitudinal depressions 1423 has a bulbed section 1460. The distal shaft 1417 also includes a reduced diameter section 1440. The reduced diameter section 1440, longitudinal grooves 1423 and bulbed section 1460 may be used to increase the surface area of the vertebral prosthesis portion 1440 that is, when implanted, within a vertebra of the spine. The increased surface area allows for more area to support the cement mantle for applications using cement or, bony ingrowth for applications using bone ingrowth. It is to be appreciated that the longitudinal grooves 1423 may also be varied as described elsewhere with regard to other grooves and, for example, as described with regard to FIGS. 13A, 13B, 6A, 6B, 6C and 5A. In addition, alternative embodiments of bend 1410 are possible as described with regard to FIGS. 7A-7D and 8A-8C.

It is to be appreciated that each of the longitudinal depressions 1423 has a longitudinally varying profile, narrowing as the longitudinal depression extends proximally. In alternative embodiments, the longitudinally varying profile can widen or remain constant as the longitudinal depression extends proximally. Although in the illustrated embodiment all of the longitudinal depressions are identical, in other embodiments, the multiple longitudinal depressions can differ, for example by having different profiles, lengths, starting and/or ending points, etc. Alternative embodiments can have one longitudinal depression, two longitudinal depressions, four longitudinal depressions, five longitudinal depressions, or more longitudinal depressions.

Figure 14C:
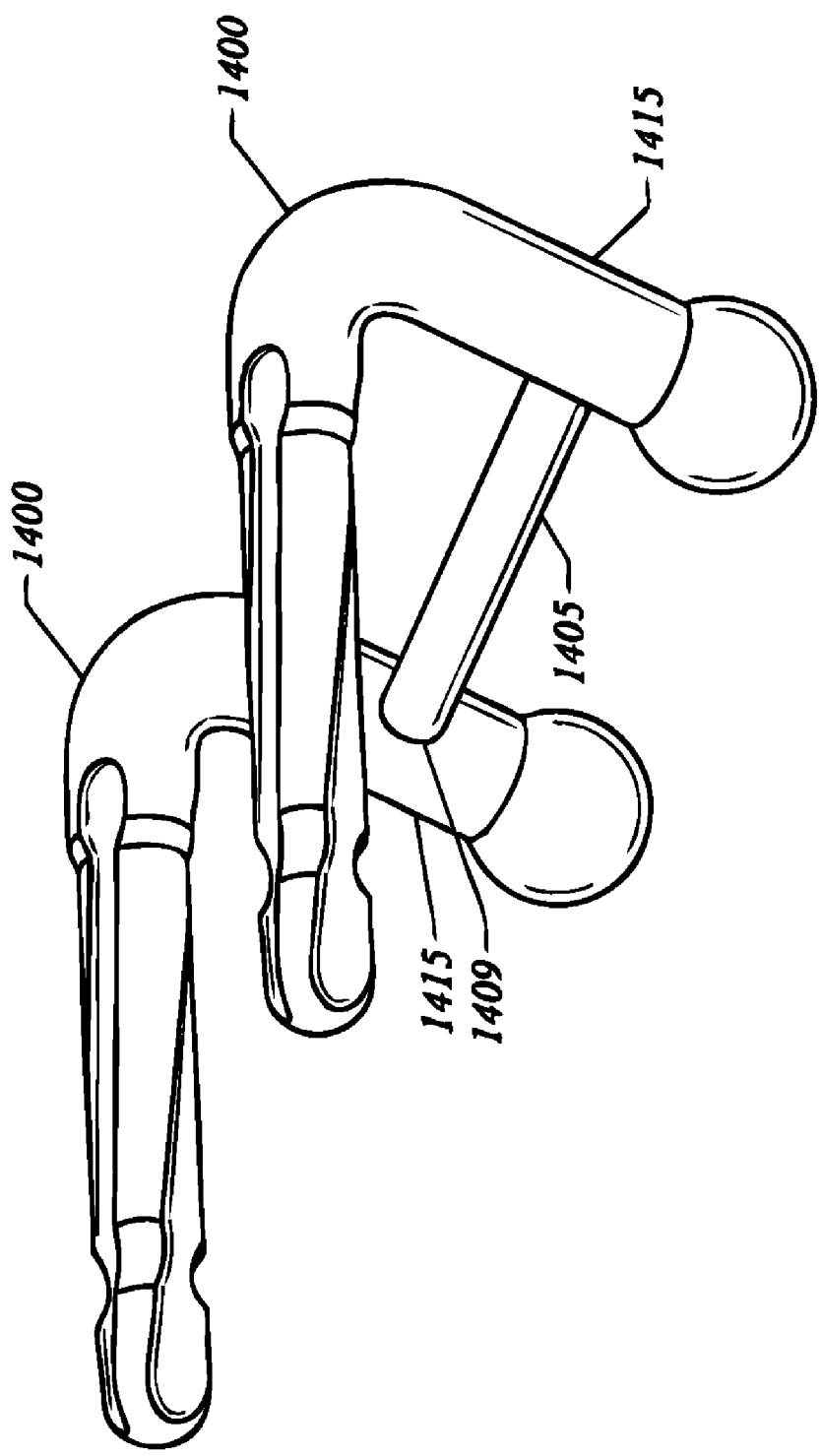
FIG. 14C provides a perspective view of a pair of vertebral prosthesis, as in FIGS. 14A and 14B, connected by a crossbar member.

FIG. 14C depicts an alternate embodiment of the vertebral prosthesis of FIGS. 14A, 14B in which a pair of prosthesis 1400 are connected by a cross-bar 1405. Cross-bar 1405 can be a cylindrical member fitting into openings 1409 in each of the shafts 1415 of the prosthesis 1400 (or can be virtually any rigid or semi-rigid member secured between the two prosthesis), and the cross-bar 1405 desirably reduces or prevents rotation of the prosthesis 1400 relative to each other. When both of the prosthesis are secured into a targeted vertebral body through the pedicles (not shown), any torsional loads experienced by an individual prosthesis 1400 will be transferred to the shaft 1415 of the opposing prosthesis by the cross-bar 1405, which will convert the torsional load to a transverse load acting on the opposing prosthesis. Desirably, the newly loaded prosthesis can resist this transverse force, thereby maintaining the entire structure in a desired position. In this embodiment, the cross-bar therefore "shares" and redistributes the torsional loading experienced by an individual prosthesis, significantly reducing the tendency for an individual prosthesis to rotate.

FIGS. 15A-15D illustrate a vertebral prosthesis portion 1500 having a plurality of grooved portions and reduced diameter portions as anti-rotation elements and anti-pullout elements. The vertebral prosthesis portion 1500 includes a proximal end 1505 and a distal end 1510. A shank 1515 is connected to the proximal end 1505. A diameter transition section 1520 is used to step down the diameter from the shank 1515 to the distal grooved section. The transition section 1520 desirably limits or eliminates potential stress concentrations or "risers" which can occur due to this geometry change. Moreover, the transition section 1520 desirably will form a tight fit with the opening formed in the bone, sealing the opening (not shown) and facilitating pressurization of cement or other supplemental fixation material within the bone without cement exiting the opening—thereby ensuring the prosthesis is well-anchored in the fixation material, if used. The vertebrae prosthesis portion 1500 includes three grooved sections: the proximal grooved section 1525 having proximal grooves 1530, the middle grooved section 1540 having middle grooves 1545 and the distal grooved section having distal grooves 1560. Additionally, there is provided a proximal reduced diameter section 1535 between the proximal grooved section 1525 and the middle grooved section 1540 and a distal reduced diameter section 1550 between the middle grooved section 1540 and the distal grooved section 1555.

In the illustrated embodiment, the grooves 1530, 1545 and 1560 are of similar size, shape and orientation. The grooves have a rounded cross section profile best seen in FIG. 15D and pronounced or sharp ridges 1565 between adjacent grooves. In addition, middle grooves 1545 and proximal grooves 1530 have a tapered width that decreases proximally. Other groove and reduced diameter configurations, cross section profile and angular orientations are possible and are described above with regard to other grooves and reduced diameter portions in other embodiments as well as described with regard to FIGS. 6A, 6B, 6C, 14A, 14B, 13A, 13B, 9A and 9B.

Figure 16A:
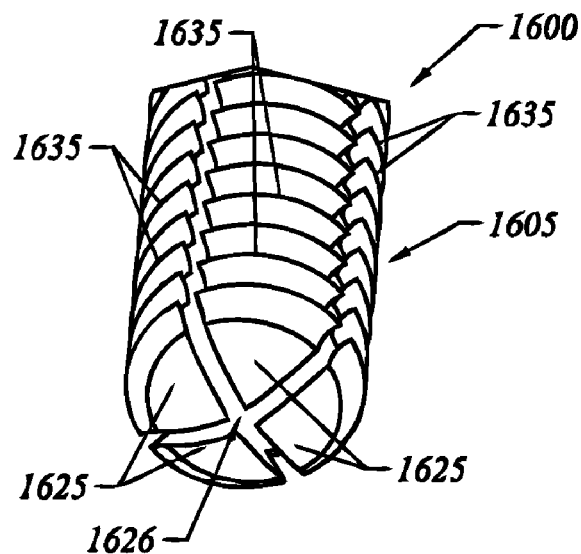
FIGS. 16A and 16B provides a perspective view of a vertebral prosthesis portion with separated members.
Figure 16B:
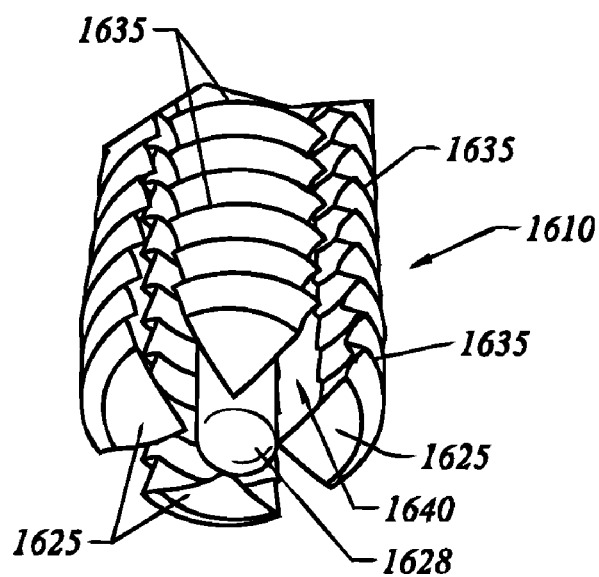

FIGS. 16A and 16B show an embodiment of a vertebral prosthesis fixation element 1600 having separable members 1625 that, when deployed as in FIG. 16B, act as anti-rotation and anti-pullout elements to compensate for forces, including torque, applied to the fixation element 1600 when used to secure intervertebral implants. The vertebral prosthesis fixation element 1600 has at least two configurations, stowed 1605 (FIG. 16A) and deployed 1610 (FIG. 16B). Vertebral prosthesis fixation element 1605 illustrates the separable members 1625 in a stowed configuration and vertebral prosthesis fixation element 1610 illustrates the separable members 1625 in a deployed configuration. The stowed configuration 1605 simplifies the transportation of the vertebral prosthesis fixation element 1600 to the implantation site by maintaining the separable members 1625 in close proximity thereby reducing the overall fixation element size. Inside of the vertebral implantation site, the separable members 1625 are placed into a deployed configuration whereby the separable member ridges 1635 are urged into contact with the surrounding vertebra. The ridges 1635 may be arranged in any orientation relative to the separable member 1625. Advantageously, when the separable members 1625 are urged into a deployed configuration 1610 and into contact with the surrounding vertebra, the size, shape, and orientation of the ridges 1635 along the separable members 1625 "dig into" or press against the surrounding material and secure the vertebral prosthesis fixation element 1600 into position. More importantly, the size, shape and orientation of the ridges 1635 provide anti-rotation and/or anti-pullout stability to the vertebral prosthesis fixation element 1600.

In the illustrated embodiments, the distal portion of the vertebral prosthesis fixation element 1600 has four separable members 1625 separated by the longitudinal hole 1626. The longitudinal hole 1626 permits a filling member 1628 to be inserted from the proximal end of the vertebral prosthesis fixation element 1600, causing the separable members 1625 to spread apart into the deployed configuration (i.e., vertebral prosthesis fixation element 1610) with deployed spacing 1640 separating adjacent separable members 1625. The exterior surface of each separable member 1625 has a plurality of continuous ridges 1635. Continuous ridges are single ridges that extend along the surface of a separable member from one spacing 1640 to the next adjacent spacing 1640. It is to be appreciated that the ridges may be segmented ridges meaning more than one ridge between adjacent spacings 1640. The ridges 1635 in the illustrated embodiment are all continuous and the ridges 1635 on each separable member 1625 are similarly oriented relative to the separable members. It is to be appreciated that other ridge configurations are possible, such as for example, combinations of continuous and segmented ridges on a single separable member, as well as different ridge orientations on the same separable member or different ridge orientations on different separable members. In addition, alternative embodiments can have more or fewer ridges than the illustrated embodiment, or be at least partly smooth.

Additionally, other embodiments of the vertebral prosthesis fixation element 1600 can have two, three, five, or more separable members 1625. The filling member can be a smooth peg as shown, or alternatively a bar, a wire, or any other shape that, upon insertion into the longitudinal hole 1626, causes the separable members 1625 to move from a stowed configuration 1605 to a deployed configuration 1610.

In one embodiment, a vertebral prosthesis fixation element 1600 is used to secure a vertebral prosthesis implanted between two vertebrae to provide restoration of movement between the vertebrae. Features of the vertebral prosthesis fixation element 1600, such as the shape, size and orientation of the ridges 1635, advantageously secure the implanted vertebral prosthesis while providing anti-rotation capability for the torques generated within the implanted prosthesis and applied to the vertebral prosthesis fixation element 1600. In another embodiment, a vertebral prosthesis fixation element 1600 is used to secure at least a portion of a vertebral prosthesis connecting two adjoining vertebrae to restore movement between the adjoining vertebrae. In this embodiment, when the separable members are in a deployed configuration, at least a portion of the ridges on at least one separable member engages the surrounding vertebrae and counteracts the forces generated by relative motion between the adjoined vertebrae, and/or the forces generated between the vertebral prosthesis and the vertebrae attached to the vertebral prosthesis.

Figure 17A:
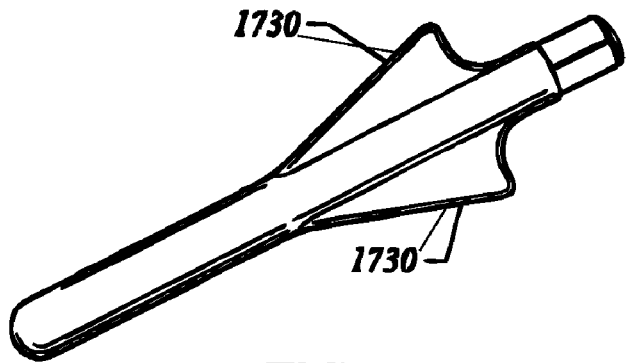
FIGS. 17A, 17B, and 17C provide a perspective view, a side view, and a distal end view, respectively, of a vertebral prosthesis portion with wings.
Figure 17B:
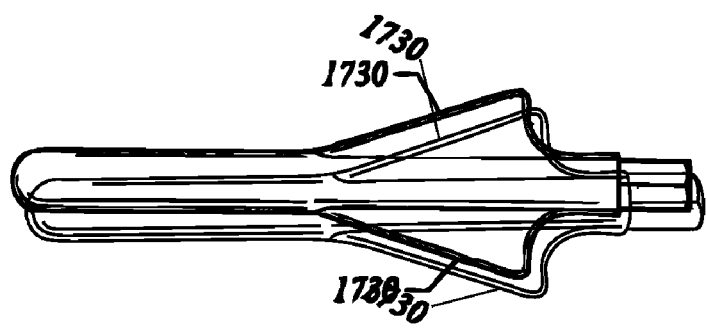
Figure 17C:
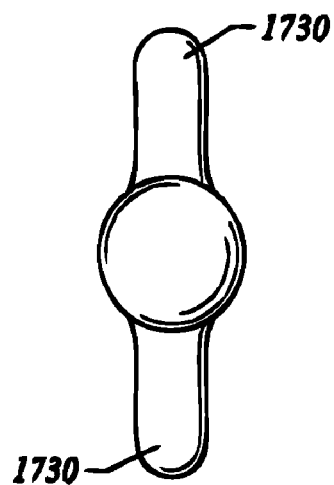

FIGS. 17A, 17B, and 17C show an embodiment of a vertebral prosthesis portion with wings as anti-rotation elements. The two wings 1730 are positioned on opposite sides of the perimeter of the fixation element, and are thus positioned apart by about 180 degrees. Alternative embodiments can have one wing, three wings, or more wings. Alternative embodiments can also employ a different amount of spacing other than 180 degrees between multiple wings for embodiments with multiple wings, and the spacing can be the same or different between the multiple wings. Although the illustrated wings 1730 have pointed triangular profiles, alternative embodiments can have rounded points, no points, and/or other profiles of other geometries, such as square, rectangular, trapezoidal, etc. In one embodiment, the wings 1730 can be sufficiently large such that the blades 1730 could fit into laterally extending slots (not shown) extending outward from to the vertebral hole that receives the fixation element.

Figure 18A:
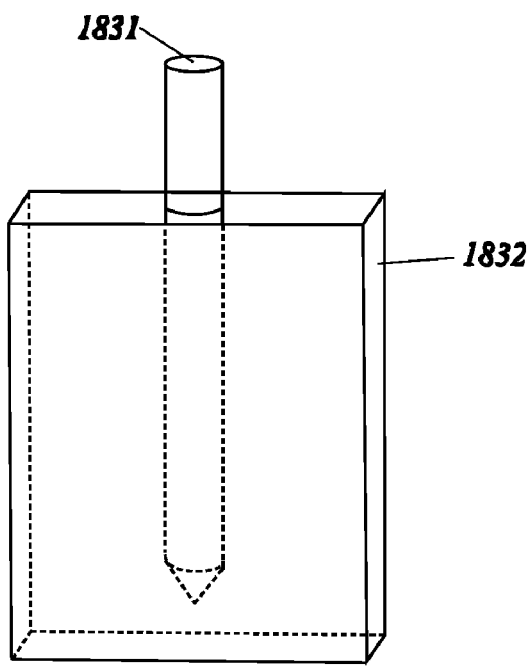
FIGS. 18A through 18F illustrate different steps in a vertebral prosthesis method for the vertebral prosthesis of FIGS. 17A through 17C.
Figure 18B:
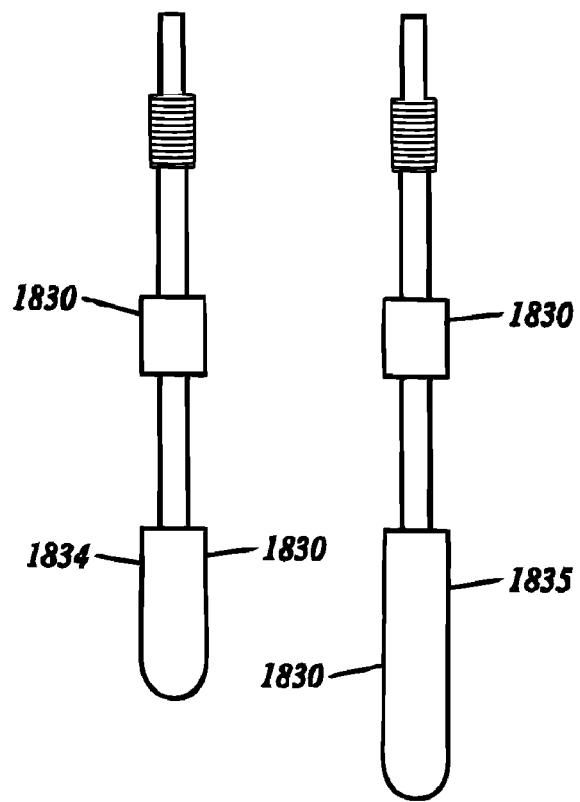
Figure 18D:
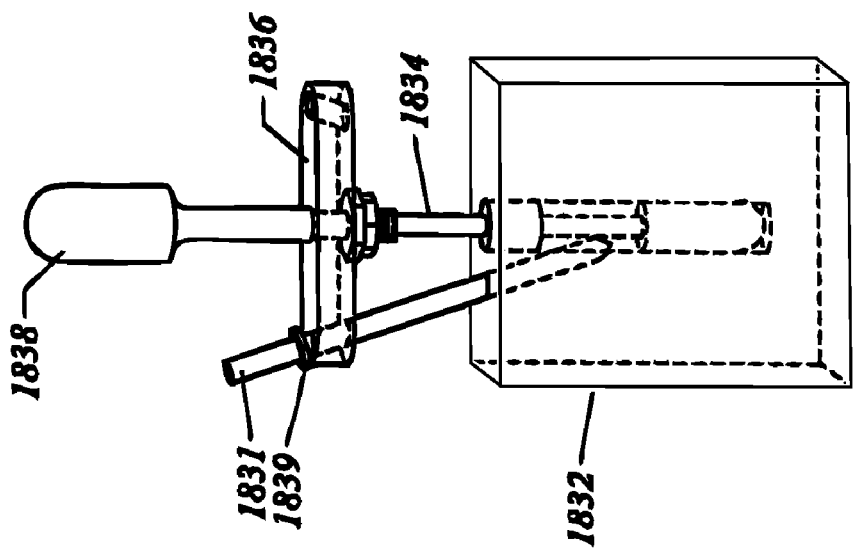
Figure 18C:
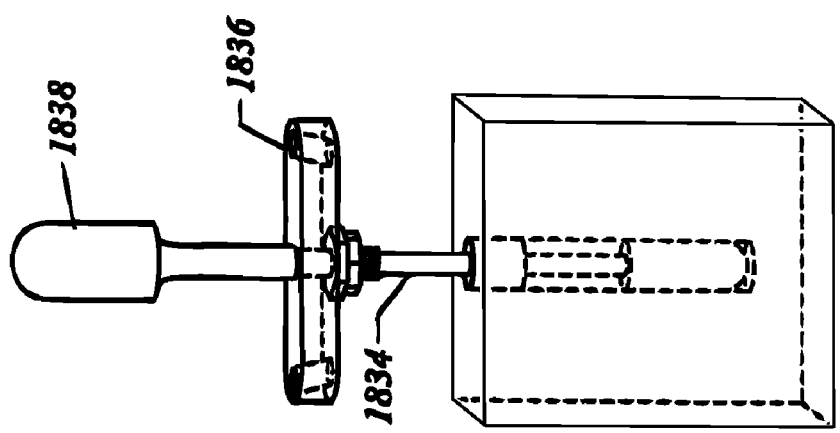
Figure 18F:
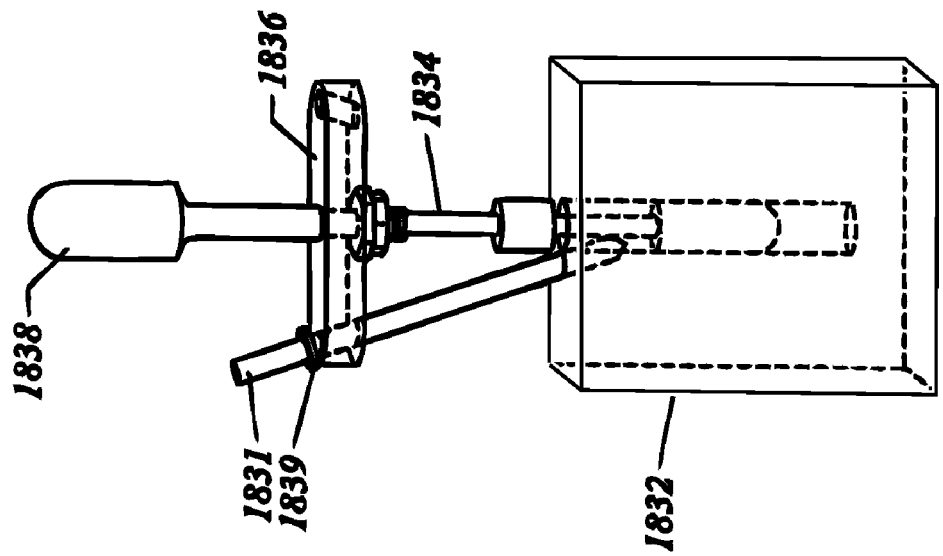
Figure 18E:
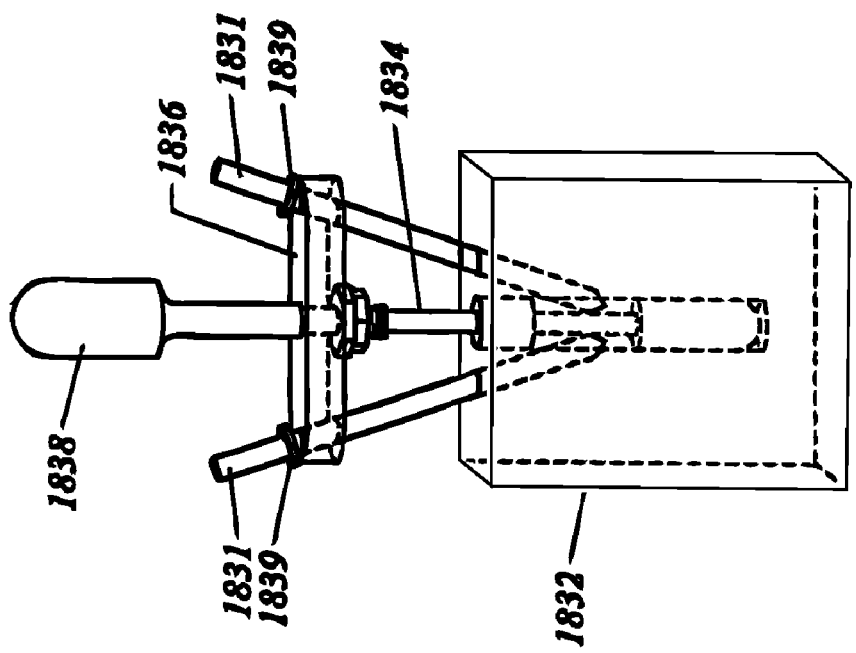

FIGS. 18A through 18F illustrate an embodiment of a vertebral prosthesis placement method for the vertebral prosthesis of FIGS. 17A through 17C. In FIG. 18A, the vertebra 1832 is perforated with a perforation tool 1831 to make a hole. The hole is large enough to receive a fixation element of a vertebral prosthesis. Although a drill is shown as the perforation tool, other perforation tools can be used, such as an auger, a laser, a broach, etc. FIG. 18B shows guide supports 1834 and 1835 of various lengths which can be chosen depending on the depth of the hole made by the perforation tool. The guide supports 1834 and 1835 are sized large enough such that the vertebra hole stabilizes the particular guide support that is inserted into the vertebra hole. For example, guide supports 1834 and 1835 can include increased-diameter sections 1830 which optimize centering in the vertebra hole. In alternative embodiments, the guide support and perforation tool can be the same, such that the perforation tool does not have to be removed after perforating the vertebra and the perforation tool also can be used as a guide support. FIG. 18C shows the guide support 1834 inserted into the hole made by the perforation tool. A perforation guide 1836 and a handle 1838 are attached to the guide support 1834. FIG. 18D shows a perforation tool 1831 guided by the perforation guide 1836. Guided by the perforation guide 1836, the vertebra 1832 is perforated with another hole. The perforation stop 1839 on the perforation tool 1831 strikes the perforation guide 1836, thereby stopping the perforation and defining the depth of that hole. FIG. 18E shows another perforation process aided by the perforation guide 1836. FIG. 18F shows that as the assembly of the handle 1838, perforation guide 1836, and guide support 1834 is removed from the vertebra, the perforation tool 1831 can be used to remove the remainder of bone from the vertebra. This can be repeated for each of the holes.

Figure 19:
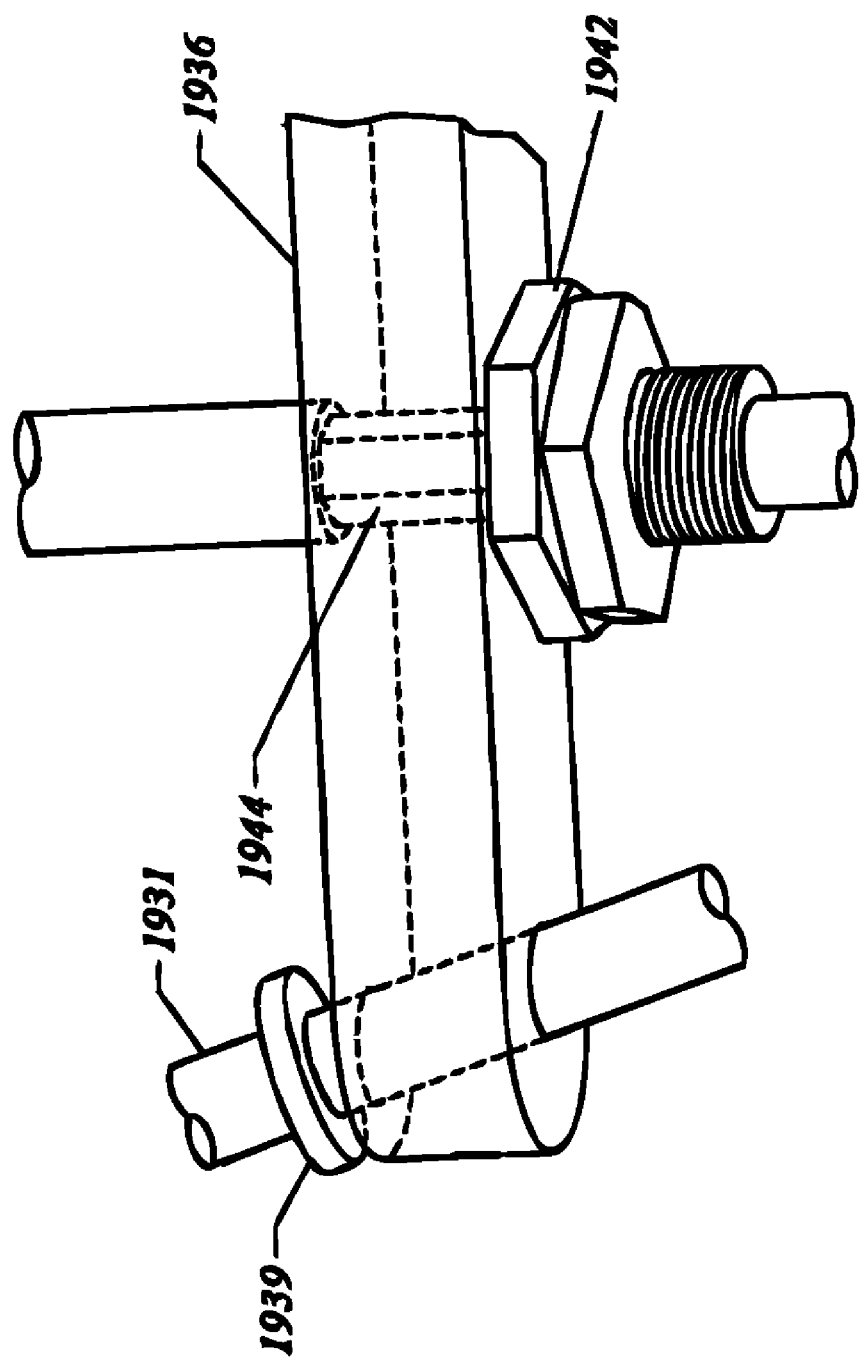
FIG. 19 is a close up view of the vertebral prosthesis tool used in the method of FIGS. 18A through 18F.

FIG. 19 is a close up view of the embodiment of the vertebral prosthesis tool used in the method of FIGS. 18A through 18F. Perforation guide 1936 has an anti-rotation flat 1944 to ensure alignment of the perforation tools 1931. Locking hex nuts 1942 allow the physician to adjust the depth of the perforation tools if necessary.

Figure 20A:
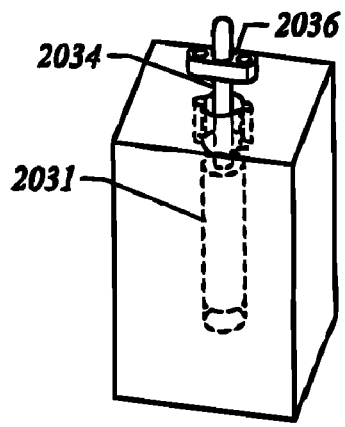
FIGS. 20A and 20B show a perspective view and a close-up view, respectively, of a vertebral prosthesis tool for a vertebral prosthesis with proximal anti-rotation features.
Figure 20B:
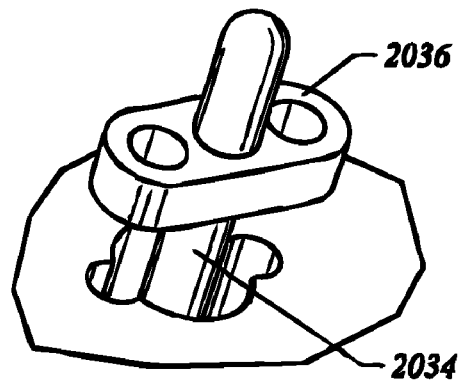

FIGS. 20A and 20B show an embodiment of a vertebral prosthesis tool for the vertebral prosthesis with proximal projections as anti-rotation elements. Perforation guide 2036 is attached to guide support 2034. In this embodiment, the guide support 2034 includes a perforation tool 2031. In alternative embodiments, the guide support and perforation tool can be distinct, such that the perforation tool is removed after perforating the vertebra, and replaced with a guide support.

Figure 21A:
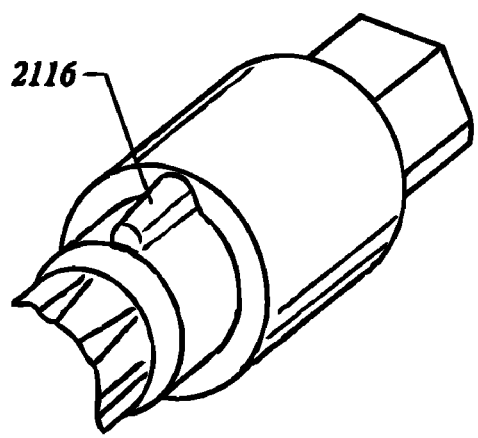
FIGS. 21A and 21B show a vertebral prosthesis portion with proximal projections, and the insertion of the prosthesis portion into a vertebra following the vertebral prosthesis tool of FIGS. 20A and 20B, respectively.
Figure 21B:
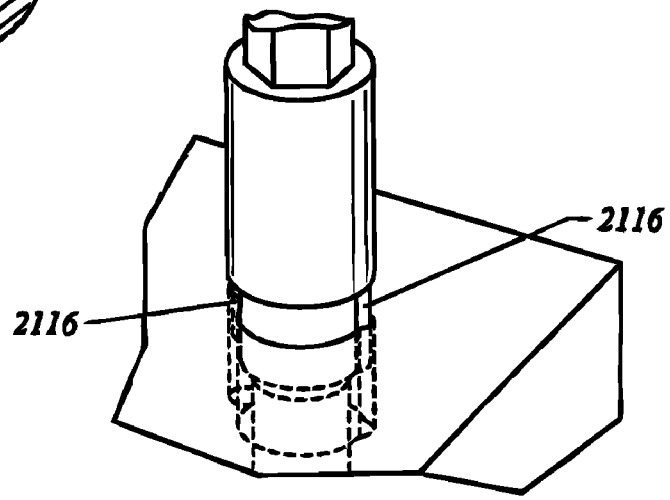

FIG. 21A shows an embodiment of a vertebral prosthesis portion with proximal projections. In alternative embodiments, the projections can be blades and/or wings. Alternative embodiments can have one projection, three projections, or more projections. The two proximal projections 2116 are positioned on opposite sides of the perimeter of the proximal portion of the fixation element, and are thus positioned apart by about 180 degrees. Alternative embodiments can also employ a different amount of spacing other than 180 degrees between multiple proximal projections for embodiments with multiple proximal projections, and the spacing can be the same or different between the multiple proximal projections. FIG. 21B shows the insertion of the prosthesis portion of FIG. 21A into a vertebra following the use of the vertebral prosthesis tool of FIGS. 20A and 20B.

Figure 22:
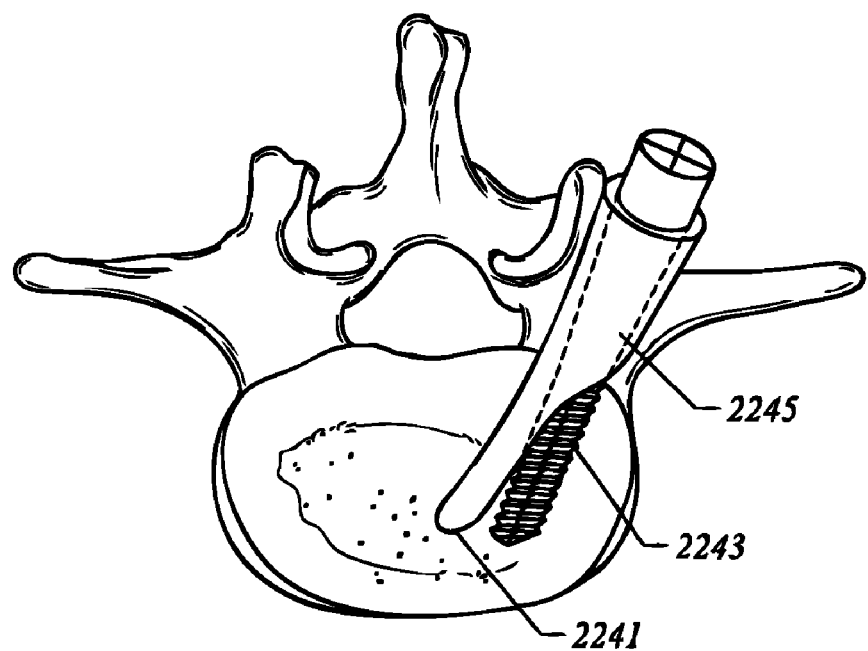
FIG. 22 is a perspective view of an installed vertebral prosthesis according to an embodiment of the invention where a fixation element is inserted into anti-rotation element.

FIG. 22 is a perspective view of an installed vertebral prosthesis according to an embodiment of the invention where a fixation element is inserted into an anti-rotation element. The anti-rotation element 2241 defines a hole, into which the fixation element 2243, shown as a screw, is inserted into. Both the hole defined by the anti-rotation element 2241 and the fixation element 2243 have a taper 2245, which can be a Morse taper, if desired. The anti-rotation element 2241 and the fixation element 2243 can thereby couple together with an interference fit when the fixation element 2243 is inserted into the anti-rotation element 2241. In various embodiments, the anti-rotation element can include a bend, or be straight; and the first fixation element can be straight, or include a bend. The bend can be sharp or gradual. In alternative embodiments, the first fixation element can define a hole into which the anti-rotation element is inserted.

Figure 23:
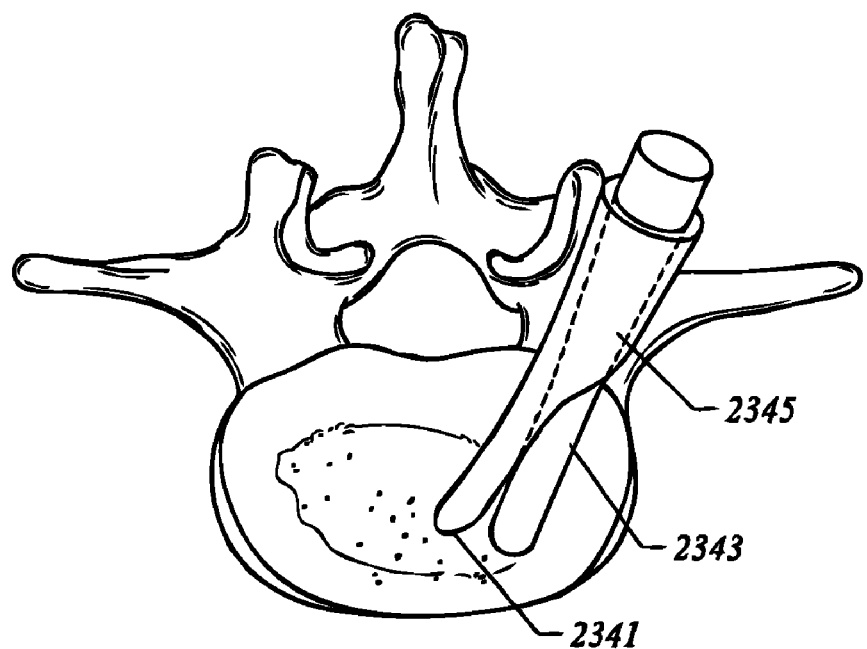
FIG. 23 is a perspective view of an installed vertebral prosthesis according to another embodiment of the invention where a fixation element is inserted into anti-rotation element.

FIG. 23 is a perspective view of an installed vertebral prosthesis according to another embodiment of the invention where a fixation element is inserted into anti-rotation element, similar to the embodiment of FIG. 22. The fixation element 2343 is a stem. In other embodiments, the fixation element and the anti-rotation element can be a corkscrew, wire, staple, adhesive, bone, and other materials known in the prosthetic arts.

Figure 24:
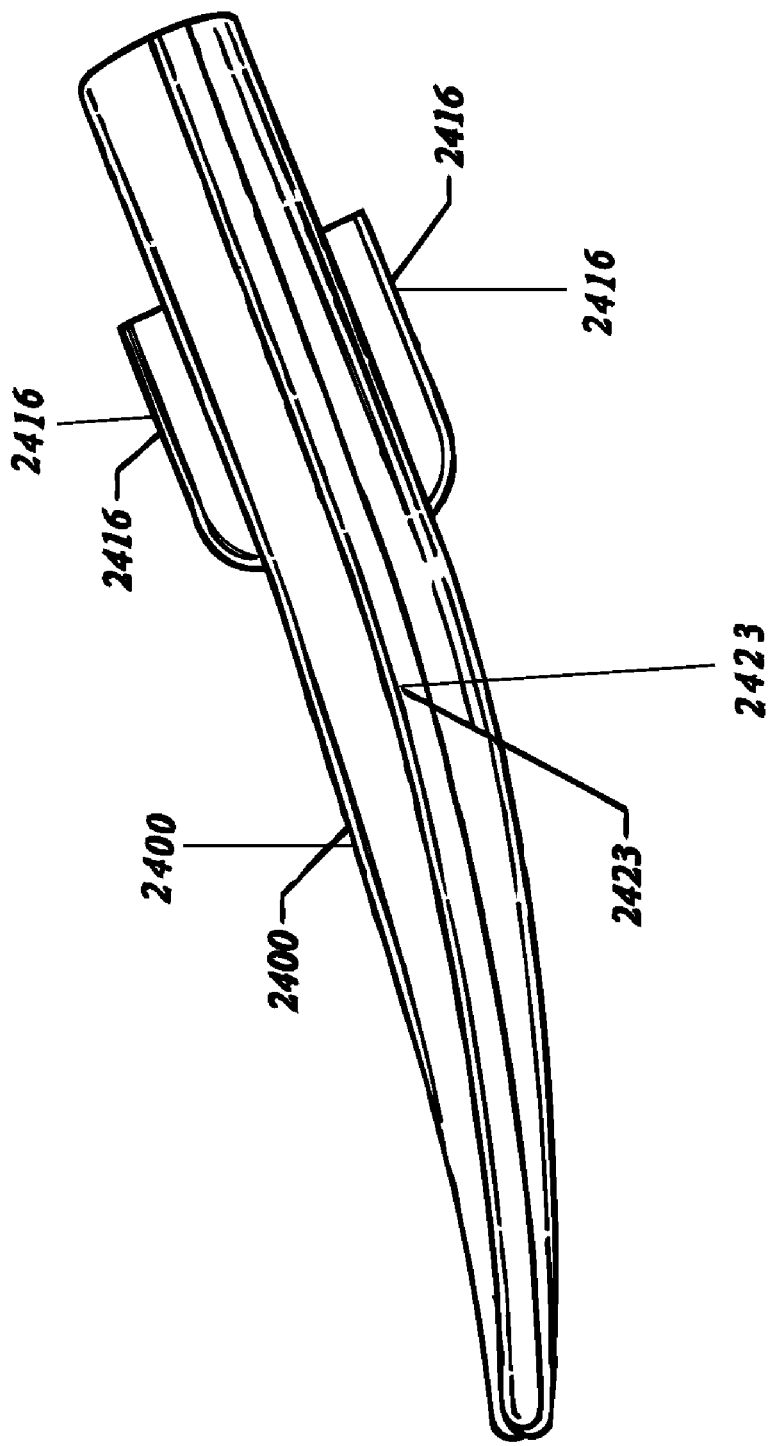
FIG. 24 is a perspective view of a vertebral prosthesis portion shaped to resist rotational force.

FIG. 24 is a perspective view of a vertebral prosthesis portion shaped to primarily resist rotational force. The shape of the fixation element 2400 has a bend. Also shown is a longitudinal depression 2423 and proximal projections 2416. Alternative embodiments can have neither the longitudinal depression 2423 nor the proximal projections 2416. Some alternative embodiments include limited anti-rotation elements, relying primarily on the non-uniform shape of the fixation element to resist rotation. Other embodiments can include anti-rotation elements other than longitudinal depressions and proximal projections.

For purposes of illustration and explanation of the anti-rotation and/or anti-pullout advantages of embodiments of the present invention, vertebral prosthesis portions have been illustrated and described in axial shaft configurations (e.g., FIGS. 6A-6C, 9A-9B, 10A, 11A-13B) and curved shaft configurations (e.g., 7A-8C, 14A-14B, and 22-24). It is to be appreciated that the anti-rotation and anti-pull out embodiments described in each are not limited to only the illustrated and described embodiments but are applicable to other different embodiments, as a substitute to or combination with the described and illustrated embodiment. For clarity, the various embodiments of the invention have been referred to as portions of a vertebral prosthesis having anti-rotation and/or anti-pull out elements. It is to be appreciated that while these elements provide the additional advantages described herein, these elements are also fasteners that act generally to secure the various loading elements and components of the prosthesis to the spine.

While preferred embodiments of the invention have been illustrated and described, it will be appreciated that various changes can be made therein without departing from the spirit and scope of the invention.

What is claimed is:

1. A vertebral prosthesis, comprising:
   a first bearing element shaped to form a portion of a facet joint;
   a first fixation element adapted to be coupled to the first bearing element, the first fixation element adapted to be inserted into a first hole formed in a vertebra; the first fixation element having a first longitudinal axis;
   a second fixation element adapted to be inserted into a second hole formed in the vertebra; the second fixation element having a second longitudinal axis;
   the first fixation element having a first anti-rotation element configured to be coupled to at least a portion of the vertebra, the first anti-rotation element extending outward from the first longitudinal axis and adapted to resist a rotational force applied to the first fixation element; and
   a cross-arm element removably connecting the first fixation element to the second fixation element.

2. The vertebral prosthesis of claim 1, further comprising: a second anti-rotation element configured to be coupled to at least a portion of the vertebra, the second anti-rotation element extending outward from the second longitudinal axis and adapted to resist a rotational force applied to the second fixation element.

3. The vertebral prosthesis of claim 1, further comprising: a bony in-growth surface on at least part of the first fixation element.

4. The vertebral prosthesis of claim 1, wherein the first anti-rotation element comprises a protrusion extending outward from the first longitudinal axis.

5. The vertebral prosthesis of claim 4, wherein the protrusion is formed integrally with the first fixation element.

6. The vertebral prosthesis of claim 1, wherein the first anti-rotation element comprises a blade extending outward from the first longitudinal axis.

7. The vertebral prosthesis of claim 1, wherein the first antirotation element comprises a rib extending outward from the first longitudinal axis.

8. The vertebral prosthesis of claim 1, wherein the first anti-rotation element comprises a longitudinal depression extending along the first longitudinal axis.

9. The vertebral prosthesis of claim 1, wherein the first anti-rotation element comprises an elongated ridge extending outward from the first longitudinal axis.

10. The vertebral prosthesis of claim 1, further comprising a first recess formed in the first fixation element, and wherein at least a portion of the cross-arm element is disposed within the first recess.

11. A vertebral prosthesis, comprising:
a first articulating surface shaped to form a portion of a facet joint;
a first fixation element adapted to be coupled to the first articulating surface, the first fixation element adapted to be inserted into a first opening formed in a vertebra; the first fixation element having a first longitudinal axis;
a second fixation element adapted to be inserted into a second opening formed in the vertebra; the second fixation element having a second longitudinal axis;
the first fixation element having a first anti-rotation element configured to be coupled to at least a portion of the vertebra, the first anti-rotation element extending outward from the first longitudinal axis and adapted to resist a rotational force applied to the first fixation element when the first fixation element is first implanted into the first opening;
a second anti-rotation element configured to be coupled to at least a portion of the vertebra, the second anti-rotation element extending outward from the second longitudinal axis and adapted to resist a rotational force applied to the second fixation element when the second fixation element is first implanted into the second opening; and
a modular cross-arm element removably connecting the first fixation element to the second fixation element.

12. The vertebral prosthesis of claim 11, wherein the first and second fixation elements are configured to be located cephalad to the modular cross-arm element when the prosthesis is surgically implanted.

13. The vertebral prosthesis of claim 11, wherein the first and second fixation elements are configured to be located cephalad to the first articulating element when the prosthesis is surgically implanted.

14. The vertebral prosthesis of claim 11, wherein a first recess is located between the first fixation element and the first articulating surface.

15. The vertebral prosthesis of claim 11, wherein substantially all of the modular cross-arm element is located between the first and second fixation elements.

16. The vertebral prosthesis of claim 11, wherein the modular crossarm element comprises a substantially cylindrical body.

17. A vertebral prosthesis, comprising:
a first bearing element shaped to form a portion of a facet joint;
a first fixation element adapted to be coupled to the first bearing element, the first fixation element adapted to be inserted into a first hole formed in a vertebra; the first fixation element having a first longitudinal axis;
a second fixation element adapted to be inserted into a second hole formed in the vertebra; the second fixation element having a second longitudinal axis;
the first fixation element having a first anti-rotation element configured to be coupled to at least a portion of the vertebra, the first anti-rotation element extending outward from the first longitudinal axis and adapted to resist a rotational force applied to the first fixation element; and
a cross-arm element removably connecting the first bearing element to a second bearing element.

18. The vertebral prosthesis of claim 17, wherein the first anti-rotation element comprises a protrusion extending outward from the first longitudinal axis.

19. The vertebral prosthesis of claim 17, wherein the first anti-rotation element comprises a blade extending outward from the first longitudinal axis.

20. The vertebral prosthesis of claim 17, wherein the first anti-rotation element comprises a rib extending outward from the first longitudinal axis.

* * * * *